US008361494B2

(12) United States Patent
Chen et al.

(10) Patent No.: US 8,361,494 B2
(45) Date of Patent: Jan. 29, 2013

(54) BIOMIMETIC IRON-OXIDE-CONTAINING LIPOPROTEIN AND RELATED MATERIALS

(75) Inventors: I-Wei Chen, Swarthmore, PA (US); Hoon Choi, Newtown Square, PA (US)

(73) Assignee: The Trustees Of The University of Pennsylvania, Philadelphia, PA (US)

( * ) Notice: Subject to any disclaimer, the term of this patent is extended or adjusted under 35 U.S.C. 154(b) by 1081 days.

(21) Appl. No.: 12/282,308

(22) PCT Filed: Mar. 6, 2007

(86) PCT No.: PCT/US2007/063413
§ 371 (c)(1),
(2), (4) Date: Sep. 9, 2008

(87) PCT Pub. No.: WO2007/106683
PCT Pub. Date: Sep. 20, 2007

(65) Prior Publication Data
US 2009/0035223 A1    Feb. 5, 2009

Related U.S. Application Data

(60) Provisional application No. 60/781,134, filed on Mar. 10, 2006.

(51) Int. Cl.
*A61K 9/127* (2006.01)
*A61K 49/18* (2006.01)

(52) U.S. Cl. ............... 424/450; 424/1.21; 424/9.321; 424/9.361

(58) Field of Classification Search .............. None
See application file for complete search history.

(56) References Cited

U.S. PATENT DOCUMENTS

| | | | |
|---|---|---|---|
| 4,452,773 A | 6/1984 | Molday | |
| 4,647,445 A | 3/1987 | Lees | |
| 5,464,696 A * | 11/1995 | Tournier et al. | 428/403 |
| 5,948,756 A | 9/1999 | Barenholz et al. | |
| 6,057,347 A | 5/2000 | Garvey et al. | |
| 6,197,809 B1 | 3/2001 | Strelchenok | |
| 6,368,619 B1 * | 4/2002 | New et al. | 424/450 |
| 6,645,463 B1 | 11/2003 | Counsell et al. | |
| 2004/0081688 A1 | 4/2004 | Del Curto et al. | |
| 2004/0234588 A1 | 11/2004 | Lu et al. | |
| 2005/0130167 A1 | 6/2005 | Bao et al. | |

FOREIGN PATENT DOCUMENTS

| | | |
|---|---|---|
| WO | 9001295 A1 | 2/1990 |
| WO | 2006073419 A2 | 7/2006 |

OTHER PUBLICATIONS

Entry for 'polyethylene glycol'. 2011 Society of Plastics Engineers website. <http://www.4spe.org/plastics-encyclopedia/polyethylene-glycol>. Accessed May 18, 2012.*
Davis, R.A. et al., Structure, assembly and secretion of lipoproteins, Biochemistry of Lipids, Lipoproteins and Membranes, Elsevier 17:473-493 (1996).
Sipkins, D.A. et al. ICAM-i expression in autoimmune encephalitis visualized using magnetic resonance imaging, JNeuroimmunol 104, 1-9 (2000).
Anderson, S.A. et al., Magnetic Resonance Contrast Enhancement of Neovasculature With avb3-Targeted Nanoparticles, Magnetic Resonance in Medicine, 44(3):433-9 (Sep. 2000).
M.Hammel, et al., "Structural characterization of nucleoside loaded low density lipoprotein as a main criterion for the applicability as drug delivery system," Chem. Phys. Lipid. 123,103-207 (2003).
R.C. Pittman, et al. "Synthetic High Density Lipoprotein Particles," J. Bio. Chem. 262[6]2435-2442 (1987).
S. Sun et al. "Size-controlled synthesis of magnetite nanoparticles," J. Am. Chem. Soc., 124, 8204-8205, (2002).
M. Krieger, et al. "Reconstituted low density Lipoprotein: a vehicle for the delivery of hydrophobic fluorescent probes to cells," JSS 10, 467-478 (1979).
Salata, J., Applications of nanoparticles in biology and medicine, J. Nanobiotechnology, 2004, 6 p., 2(3).
Zheng et al., Tricarbocyanine Cholesteryl Laurates Labeled LDL: New Near Infrared Fluorescent Probes (NIRFs) for Monitoring Tumors and Gene Therapy of Familial hypercholesterolemia, Bioorg. & Med. Chem. Lett. 12:1485-1488 (2002).
Zheng et al., "Rerouting lipoprotein nanoparticles to selected alternate receptors for the targeted delivery of cancer diagnostic and therapeutic agents", PNAS, vol. 102, No. 49 (2005), pp. 17757-17762.
International Search Report for PCT/US07/63413, Oct. 29, 2007.

* cited by examiner

*Primary Examiner* — Michael G Hartley
*Assistant Examiner* — Jennifer Lamberski
(74) *Attorney, Agent, or Firm* — RatnerPrestia

(57) ABSTRACT

An engineered lipoprotein including (a) a core particle or a plurality of core particles, each core particle has (i) an inner part comprising a hydrophilic active agent and a hydrophilic portion of an amphiphilic cholesterol and (ii) an outer part including a hydrophobic portion of the amphiphilic cholesterol, (b) a layer surrounding the core particle or a plurality of core particles, the layer includes a phospholipid, (c) an apoprotein associated with the layer, and optionally, (d) a homing molecule associated with at least one of the apoprotein or the phospholipid.

10 Claims, 10 Drawing Sheets

BIOMIMETIC IRON-OXIDE-CONTAINING LIPOPROTEIN AND RELATED MATERIALS

BACKGROUND OF THE INVENTION

1. Field of Invention

This invention relates to a non-naturally occurring lipoprotein composite containing an MRI contrast agent or a therapeutic substance in its core.

2. Description of Related Art

Lipoproteins are macromolecular composites formed by lipids and proteins at different ratios, sizes and densities. Lipoproteins transport water-insoluble lipids (e.g., cholesterol) in the blood. Lipoproteins comprise an apolar core surrounded by a phospholipid monolayer containing unesterified cholesterol and apolipoproteins. The five main lipoprotein classes include chylomicrons (75-1200 nm), very-low-density lipoprotein (30-80 nm), intermediate-low-density lipoprotein (25-35 nm), low-density lipoprotein (LDL) (18-25 nm) and high-density lipoprotein (HDL) (8-12 nm) (see Vance, D. E., Vance J E (eds.) (1996) *Elsevier* 31).

Lipoproteins are good candidates for drug delivery or imaging because they are not recognized as foreign entities by the human immune system and escape absorption by the reticuloendothelial system (see U.S. Pat. No. 5,948,756 to Barenholz et al.).

Zheng, et al. studied rerouting lipoprotein nanoparticles to selected alternate receptors for the targeted delivery of cancer diagnostic and therapeutic agents (see PNAS 102[40] 17752-17762 (2005)). A lipoprotein-based nanoplatform (LBNP) was generated by conjugating tumor homing molecules to the protein components of naturally occurring lipoproteins, wherein a low-density lipoprotein (LDL) folate receptor (FR)-targeted agent was prepared by conjugating folic acid to lysine residues of the apoB-100 protein, which is an apolipoprotein. The article describes reconstituting the lipid core reconstituted with a lipophilic photodynamic therapy agent tetra-t-butyl-silicon phthalocyanine bisoleate (SiPc-BOA).

An example of natural lipoprotein is low-density lipoprotein (LDL). The low-density lipoprotein (LDL) particle contains a lipid core of some 1500 esterified cholesterol molecules and triglycerides. A shell of phospholipids and unesterified cholesterol surrounds this highly hydrophobic core. The shell also contains a single copy of apoB-100, which is recognized by the LDL receptor (LDLR).

Zheng, et al. developed various reconstituted LDL, i.e., natural LDL with a modified core/shell to incorporate imaging agents. Another method developed by Zheng, et al. is to form a phospholipid micelle that is further decorated by an apolipoprotein (or apoprotein, used interchangeably hereafter), which renders it LDL-like. These methods can be extended beyond LDL to other members of the cholesterol family. The advantage of LDL or LDL-like entity as a delivery vehicle lies in its intrinsic biocompatibility and richness of variety. The surface of the entity can be further modified, by ligand or antibody, to make it target-specific.

International Application Publication No. WO 2006/073419 to Zheng et al. discloses non-naturally occurring lipoprotein nanoplatforms ("LBNP") that allow targeted delivery of active agents and can be used to create a diverse set of multifunctional cancer diagnostic and therapeutic devices.

Diverse targeting is achieved by conjugating certain tumor-homing molecules (e.g., folic acid) to the Lys residues exposed on the apoB-100 surface optionally followed by capping the remaining unreacted Lys residues. LDLR binding is turned off and the modified LDL particles are redirected to the desired cancer signatures and/or specific tissues, i.e., molecules that are selectively overexpressed in various types of cancer cells. In particular embodiments, the multifunctionality of LBNP provides targeted delivery of active agents e.g., diagnostic and/or therapeutic agents. Such diagnostic agents include magnetic resonance imaging (MRI) agents, near-infrared fluorescence (NIRF) probes and photodynamic therapy (PDT) agents.

High-resolution contrast enhanced magnetic resonance imaging (MRI) is one of the most useful techniques for screening tumors and other anatomical abnormalities. In MRI, an image of an organ or tissue is obtained by placing a subject in a strong magnetic field and observing the interactions between the magnetic spins of the protons and radiofrequency electromagnetic radiation.

Due to sensitivity limitation of the current MRI techniques, efficient recognition requires a very high capacity target like fibrin, which is present in sufficient quantity to be seen with simple targeted Gd chelates, or targets accessible to the blood stream that can be bound with a Gd cluster, polymer or an iron particle. This is possible presently only in a limited target set. For example, the seminal work by Sipkins et al. (Sipkins, D. A. et al. ICAM-i expression in autoimmune encephalitis visualized using magnetic resonance imaging. J Neuroimmunol 104, 1-9 (2000)) demonstrated that paramagnetic immunoliposomes targeted to the integrin receptor, intercellular adhesion molecule-i (ICAM-1), could be used to visualize altered ICAM-1 expression in autoimmune encephalitis using MRI. Lanza and Wickline et al. (Anderson, S. A. et al., Magnetic Resonance in Medicine. 2000 September; 44(3):433-9) developed a fibrin-targeted paramagnetic nanoparticle contrast agent for high-resolution MRI characterization of human thrombus. In their approach, the contrast agent is a lipid-encapsulated perfluorocarbon nanoparticle with numerous Gd-DTPA complexes incorporated into the outer surface. The nanoparticles themselves provide little or no blood-pool contrast when administrated in vivo, but when they bind and collect at a targeted site, such as a thrombus, they modify the TI-contrast of the tissue substantially. Thus, they inherently yield high signal-to-noise ratios. However, unlike imaging fibrin, an extra-cellular target, intracellular MRI imaging is particularly challenging because the minimum concentration of MRI agents required for the MRI detection limit is much higher (about 1 mM) than the extracellular target (40 µM).

WO 2006/073419 describes that diagnostic agents can be associated with a surface or a core of lipoprotein particles LBNP. Diagnostic agents such as MRI contrast agents associated with the inside of the core of LBNP are obtained by replacing cholesterol esters located inside the lipid core with lipophilic agents. WO 2006/073419 does not describe forming a core comprising a lipophobic or a hydrophilic diagnostic agent encapsulated with an amphiphilic cholesterol.

International Application Publication No. WO90/01295 to Menz et al. discloses magnetic resonance (MR) contrast agents associated with ligands which are recognized by receptor mediated endocytosis (RME). MR contrast agents are prepared by co-precipitation of superparamagnetic metal oxides with the ligands, direct conjugation with a ligand or conjugation of a ligand to a silanized superparamagnetic material.

Methods of making of lipophilic agent are described by U.S. Pat. No. 6,645,463B1 to Counsell, U.S. Pat. No. 4,647,445 to Lees, and U.S. Pat. No. 4,452,773 Molday.

Other related technologies and background are described in the following publications: M. Hammel, P. Laggner and R. Prassl "Structural characterization of nucleoside loaded low density lipoprotein as a main criterion for the applicability as drug delivery system", Chem. Phys. Lipid. 123, 103-207

(2003); R. C. Pittman, et al. "Synthetic High Density Lipoprotein Particles", J. Bio. Chem. 262[6] 2435-2442 (1987); S. Sun and H. Zeng "Size-controlled synthesis of magnetite nanoparticles", J. Am. Chem. Soc., 124, 8204-8205; M. Krieger, et al. "Reconstituted low density Lipoprotein: a vehicle for the delivery of hydrophobic fluorescent probes to cells", JSS 10, 467-478 (1979).

However, despite the current developments, there is still a need in the art to produce an engineered lipoprotein having a core with substance incorporated therein which are not limited to lipophilic substances.

All references cited herein are incorporated herein by reference in their entireties.

BRIEF SUMMARY OF THE INVENTION

In accordance with the invention, a cholesterol-coated-MRI contrast agent particle or a desired therapeutic substance containing core particle is prepared first to be used in lieu of cholesterol in the subsequent procedure of forming a lipid micelle and finally an engineered lipoprotein. Since the procedures of forming the lipid micelle (using a phospholipid surfactant) and lipoprotein particles (using apoprotein decoration) are well known, the improvement is to obtain cholesterol-coated MRI contrast agent or therapeutic substance particles which have similar physical chemical characteristics to cholesterol.

Accordingly, the invention provides an engineered lipoprotein including (a) a cholesterol-coated core particle or a plurality of cholesterol-coated core particles, each core particle has (i) an inner part comprising a hydrophilic active agent and a hydrophilic portion of an amphiphilic cholesterol and (ii) an outer part including a hydrophobic portion of the amphiphilic cholesterol, (b) a layer surrounding the core particle or a plurality of core particles, the layer includes a phospholipid, (c) an apoprotein associated with the layer, and optionally, (d) a homing molecule associated with at least one of the apoprotein or the phospholipid.

In certain embodiments, the hydrophilic active agent is at least one of a diagnostic agent or a therapeutic agent.

In certain embodiments, the diagnostic agent is an MRI contrast agent, which preferably comprises a metal group Fe, Co, Mn, Ni, or Cr. In certain embodiments, the MRI contrast agent is iron oxide.

In certain embodiments, the amphiphilic cholesterol is a member selected from the group consisting of cholesteryl 3β-N-(dimethylaminoethyl) carbamate hydrochloride, cholic acid, 3-cholesteryloxycarbonyl pentanoic acid, cholesterol-poly(ethylene glycol), cholesterol-poly(ethylene oxide) and cholesterol-poly(glucoside).

In certain embodiments, the phospholipid is a member selected from the group consisting of phosphatidylcholine, phosphatidylethanolamine, phosphatidylserine, phosphatidylinositol, phosphatidic acid, phosphatidylglycerol, and cardiolipin.

In certain embodiments, the apoprotein is a member selected from the group consisting of apoprotein A1, A2, A4, B48, B100, C1, C2, C3, D, and E.

In certain embodiments, engineered lipoprotein includes (a) the core particle or a plurality of core particles, each core particle consisting essentially of (i) an inner part consisting essentially of the hydrophilic active agent and a hydrophilic portion of an amphiphilic cholesterol and (ii) an outer part consisting essentially of the hydrophobic portion of the amphiphilic cholesterol, (b) a layer surrounding the core particle or a plurality of core particles, the layer consisting essentially of the phospholipid, (c) an apoprotein associated with the layer, and optionally, (d) a homing molecule associated with at least one of the apoprotein or the phospholipid.

Also provided is a core particle which comprises:
(i) an inner part comprising a hydrophilic active agent and a hydrophilic portion of an amphiphilic cholesterol; and
(ii) an outer part comprising a hydrophobic portion of the amphiphilic cholesterol, provided that the hydrophilic portion of the amphiphilic cholesterol is at least one of (a) an anionic group selected from at least one of sulfate, sulfonate or carboxylate anions, (b) a cationic group selected from at least one of quaternary ammonium cations, or (c) a hydrophilic nonionic group selected from at least one of poly(ethylene glycol), poly(ethylene oxide) and poly(glucoside).

In certain embodiments, the diameter of the core is from about 5 to about 1000 nanometers. In certain embodiments, a diameter of the core is from 7 to 200 nanometers.

Further provided is a high temperature method of making a core particle, the method comprising:
providing a hydrophilic active agent source;
providing an organic solvent;
providing a hydrophobic diol;
providing an amphiphilic cholesterol;
combining the hydrophilic active agent source, the organic solvent, the hydrophobic diol, and the amphiphilic cholesterol under an inert gas to form a mixture; and
heating the mixture to a temperature of about 180° C. to about 375° C. during a time interval sufficient to form the core particle.

In another aspect, the invention is a cholesterol coated core particle made by the high temperature method as described above, wherein the core has a diameter of about 5 to about 200 nanometers.

In another aspect, the invention provides an emulsion method of making a core particle, the method comprising:
providing a first water phase comprising a hydrophilic active agent source;
providing a first oil phase comprising an amphiphilic cholesterol which is a cholesterol-based surfactant;
combining the water phase and the oil phase to form a first water-in-oil emulsion;
providing a second water phase comprising an OH-source;
providing a second oil phase comprising a cholesterol-based surfactant;
combining the second water phase and the second oil phase to form a second water-in-oil emulsion;
combining the first water-in-oil emulsion with the second water-in-oil emulsion, and thereby forming the core particle.

In certain embodiments of the emulsion method, the cholesterol-based surfactant is at least one of the cholesteryl 3β-N-(dimethylaminoethyl)carbamate hydrochloride, sodium cholesteryl sulfate, cholesterol-poly(ethylene glycol), cholesterol-poly(ethylene oxide) and cholesterol-poly(glucoside).

In another aspect, the invention is a cholesterol coated core particle made by the emulsion method as described above, wherein the core has a diameter of a diameter of about 5 to about 1000 nanometers.

Further provided is a method of making an engineered lipoprotein, the method comprising:
providing the cholesterol coated core particle as described above
adding a phospholipid to the core particle or the plurality of core particles to form a phospholipid layer surrounding the core particle or the plurality of core particles and thereby forming a phospholipids micelle; and adding an apoprotein to the phospholipids micelle and thereby making the engineered lipoprotein.

In certain embodiments, the method of making an engineered lipoprotein further comprises adding a homing molecule.

In certain embodiments, the method of making an engineered lipoprotein further comprises adding a hydrophobic active agent to the core particle or the plurality of particles prior to adding the phospholipid and forming the phospholipid layer surrounding a mixture of the core particle or the plurality of core particles and the hydrophobic active agent.

Further provided is a method of using the engineered lipoprotein of the invention, the method comprising administering the engineered lipoprotein to the cell or the tissue and thereby causing the engineered lipoprotein to bind to a selected receptor on the cell or the tissue, and monitoring the engineered lipoprotein position in a cell by recording a signal detectable by MRI.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figure 1A:
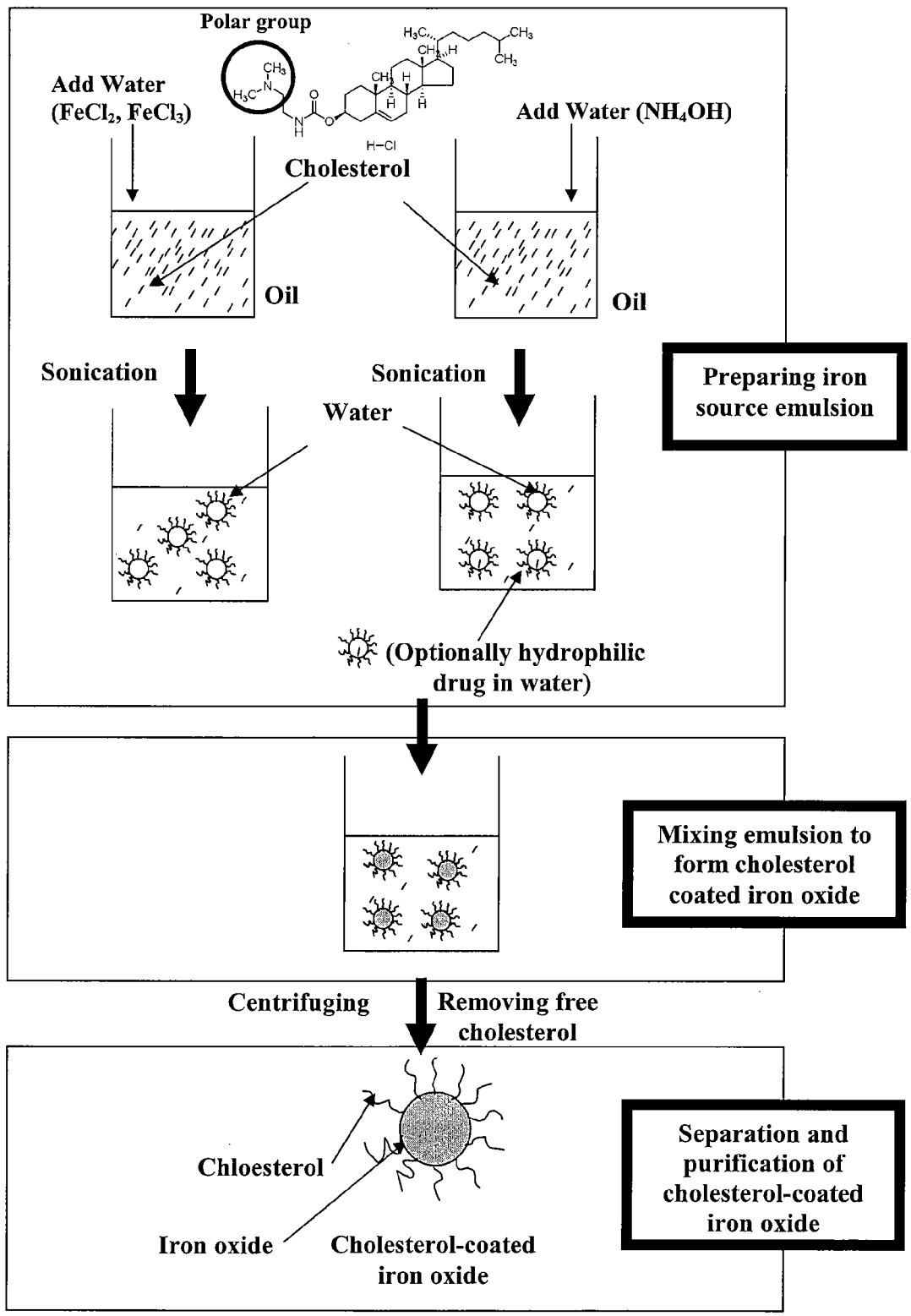
FIGS. 1A and 1B are a scheme demonstrating the method of making reconstituted lipoprotein with a cholesterol coated iron oxide core, wherein the coated core was obtain by reacting two emulsions.

This invention is based on the discovery that a lipoprotein based composite or an engineered lipoprotein can be used as a vehicle for delivering a hydrophilic active agent (e.g., an imaging or diagnostic agent or another desired therapeutic substance) to a targeted location, wherein hydrophilic active agent is encapsulated by amphiphilic cholesterol.

Previously described methods of making or modifying the core of a lipoprotein involved combining or replacing lipophilic substances of the core, e.g., esterified cholesterol and triglycerides, with other desired lipophilic substances. The modified core was then encapsulated in a layer of amphiphilic and/or polar lipids (lipids that are more polar than the outer core cholesterol), e.g., phospholipids.

In this invention, amphiphilic cholesterol is used as a core particle forming material. Inventors have discovered that using amphiphilic cholesterol as a core particle forming material instead of weakly polar cholesterol allows to encapsulate a hydrophilic active agent such that the polar group of amphiphilic cholesterol is incorporated into the inner surface of the core and is entangled with the hydrophilic active agent, and the remaining non-polar body of amphiphilic cholesterol is repelled from the core's inner surface and forms a cholesterol based outer shell, which can be in turn encapsulated by a shell of phospholipids (see FIGS. 1A-1B). The core of the engineered lipoprotein of the invention is a cholesterol-coated hydrophilic active agent particle, which can then be suspended in the oily solution.

Advantageously, the resulting cholesterol-coated hydrophilic active agent particle suspension is essentially indistinguishable from a cholesterol suspension without the hydrophilic active agent and may therefore be used to form lipoprotein in the same way as cholesterol has been used. In this invention, amphiphilic cholesterol is not covalently bound or fused with the hydrophilic active agent.

The engineered lipoprotein of the invention has several structural components: (a) a core particle or a plurality of core particles, each core particle having (i) an inner part comprising a hydrophilic active agent and a hydrophilic portion of an amphiphilic cholesterol and (ii) an outer part comprising a hydrophobic portion of the amphiphilic cholesterol; (b) a layer surrounding the core particle or a plurality of core particles, the layer comprising a phospholipid; (c) an apoprotein associated with the layer, and optionally, (d) a homing molecule associated with at least one of the apoprotein or the phospholipid. In certain embodiments, the presence of homing molecules is required. In this invention, the term "a core particle" is used interchangeably with the term "cholesterol coated core particle."

Further provided is an engineered lipoprotein which includes (a) the core particle or a plurality of core particles, each core particle consisting essentially of (i) an inner part consisting essentially of the hydrophilic active agent and a hydrophilic portion of an amphiphilic cholesterol and (ii) an outer part consisting essentially of the hydrophobic portion of the amphiphilic cholesterol, (b) a layer surrounding the core particle or a plurality of core particles, the layer consisting essentially of the phospholipid, (c) an apoprotein associated with the layer, and optionally, (d) a homing molecule associated with at least one of the apoprotein or the phospholipid.

Hydrophilic Active Agent

In the core particle, the hydrophilic active agent is wrapped in or coated with the amphiphilic cholesterol such that the outer part of the core is made of the non-polar part of the cholesterol and is hydrophobic.

The term "hydrophilic active agent" as used herein means a diagnostic or a therapeutic hydrophilic agent, which may be a natural or synthetic biomolecule, a nucleic acid or gene, a liquid, a crystalline or amorphous solid particle or a substance, which may be organic, inorganic or metallic. The term "a diagnostic agent" is used interchangeably herein with the term "an imaging agent".

Preferred imaging agent is an MRI contrast agent. The MRI contrast agents are known in the art (see for example, WO90/01295 to Menz et al.) and can be characterized as paramagnetic, ferromagnetic, and superparamagnetic materials.

MRI contrast agents preferably contain metals such as Fe, Co, Mn, Ni, Cr in divalent and trivalent oxidation states, wherein Fe(III), Co, and Mn are most preferred. Non-limiting examples of MRI contrast agents suitable for making the engineered lipoprotein of the invention include MnO, CoO, $Fe_2O_3$, $Fe_3O_4$, $MnFe_2O_4$, and $CoFe_2O_4$. Methods of making MRI contrast agent are known in the art.

In addition to the imaging agent, any hydrophilic therapeutic substance can be incorporated into the core. In a situation where the therapeutic substance is delicate and can not be heated, the emulsion process utilizing low temperature can be used.

The high temperature process can be used if the incorporation of an inorganic therapeutic substance or a substance that is capable of withstanding such temperatures is desired. Such substances can be useful for hyperthermia (a tumor destruction process utilizing heating) wherein a local heating source is introduced at the cancerous cell, and this source receives radiation from outside generating heat to destroy cancerous cells (see Salata, J Nonobiotechnology 2004, 2:3 referencing Yoshida et al, Magn Magm Mater 1999, 194:176-184).

The term "therapeutic agent" as used herein includes a drug, a biomolecule, a radioactive element, or a substance which accepts external radiation to heat up locally to destroy diseased cells. This invention provides a method to encapsulate hydrophilic therapeutic substance in the cholesterol core by using amphiphilic cholesterols. The therapeutic agent can also be the same as an imaging agent. For example, the MRI agent can be used for treating conditions such as, for example, hyperthermia, wherein it can be used to attach to, identify and heat/destroy tumorous cells.

If the imaging or therapeutic agent is hydrophobic, it can still be incorporated with the cholesterol core because it is miscible with the non-polar part of the amphiphilic cholesterol, which is encapsulated in the phospholipid monolayer. For example, during the addition of phospholipid, cholesterol-coated hydrophilic active agent (e.g., iron oxide) and phospholipid are suspended in an oily solution. To this solution a hydrophobic imaging or therapeutic agent can be conveniently added. After drying this mixture to remove the oily solution, water is added that will form micelles with phospholipid monolayer as a shell and cholesterol-coated hydrophilic active agent and the hydrophobic agent encapsulated inside the shell. The remaining process of introducing apoprotein then proceeds as before.

The therapeutic agents useful in this invention are known in the art and may contain any synthetic or natural biomolecules, or inorganic (metallic or ceramic) particles. They are intended for delivering biochemical or physical effects (heat, radiation, mechanical vibration, etc.) to the diseased organs or cells to seek altering or destruction of cells or their functions.

Several different species of imaging agents/therapeutic agents can be used simultaneously.

Amphiphilic Cholesterol

The term "amphiphilic cholesterol" as used herein refers to a molecule having a polar, water-soluble group attached to a nonpolar, water-insoluble body of cholesterol. Addition of polar groups is intended to increase hydrophilicity of cholesterol beyond week polarity that which is based on the existing OH group at the position of carbon atom number three.

Amphiphilic cholesterol of the invention consists of hydrophilic portion and a hydrophobic portion.

The hydrophilic portion of the amphiphilic cholesterol is a polar groups or a plurality of groups which are added to the tail end of the cholesterol molecule. For the purposes of this invention, the term "group" is inclusive of a molecule such as, for example, a polymer, which confers desired polarity. The hydrophilic portion of the amphiphilic cholesterol is at least one of (a) an anionic group selected from at least one of sulfate, sulfonate or carboxylate anions, (b) a cationic group selected from at least one of quaternary ammonium cations, or (c) a hydrophilic nonionic group selected from at least one of poly(ethylene glycol), alkyl poly(ethylene oxide) and alkyl poly(glucoside).

The hydrophobic portion of the amphiphilic cholesterol includes the rest of the molecule such as the four ring structure and the tail portion minus the polar group(s).

The term "amphiphilic cholesterol" of the invention is inclusive any polar derivatives of cholesterol, for example, bile acids, bile salts, and cholesterol-based surfactant.

Non-limiting examples of amphiphilic cholesterol include cholesteryl 3β-N-(dimethylaminoethyl) carbamate hydrochloride, cholic acid, 3-cholesteryloxycarbonyl pentanoic acid, cholesterol-poly(ethylene glycol), cholesterol-poly(ethylene oxide) and cholesterol-poly(glucoside).

Amphiphilic cholesterol is commercially available, and methods of making amphiphilic cholesterol are known in the art.

Phospholipids

Phospholipids

Phospholipids are used in this invention to form a shell encapsulating the cholesterol-coated hydrophilic active agent particle and thereby forming the engineered lipoprotein of the invention. Other amphiphilic and/or polar lipids, which are more polar than the cholesterol coating can be used alone or in combination with phospholipids. Non-limiting examples of phospholipids include phosphatidylcholine, lysophosphatidyicholine, phosphatidylethanolamine, phosphatidylserine, phosphatidylinositol, as well as combinations thereof.

Lipoprotein Particles

Lipoprotein particles are a class of naturally occurring nanostructures. Cholesterol and triacyiglycerols are transported in body fluids in the form of lipoprotein particles. Each particle consists of a core of hydrophobic lipids surrounded by a shell of more polar lipids and proteins. The protein components of these macromolecular aggregates have two roles: they solubilize hydrophobic lipids and contain cell-targeting signals. Lipoprotein particles are classified according to increasing density: chylomicrons, chylomicron remnants, very low density lipoprotein (VLDL), intermediate-density lipoproteins (IDL), low-density lipoprotein (LDL), and high density lipoproteins (HDL). Accordingly, each of them is different in size, and most of them have nanostructures (<100 nm) with the exception of chylomicrons and chylomicron remnants.

Low Density Lipoprotein (LDL) Particles

LDL is the principal carrier of cholesterol in human plasma and delivers exogenous cholesterol to cells by endocytosis via the LDLR.

The LDL particle is a naturally occurring nanostructure typically with a diameter of 22 nm. It contains a lipid core of some 1500 esterified cholesterol molecules and triglycerides. A shell of phospholipids and unesterified cholesterol surrounds this highly hydrophobic core. The shell also contains a single copy of apoB-100, which is recognized by the LDLR.

High Density Lipoprotein (HDL) Particles

Plasma HDL is a small, spherical, dense lipid-protein complex that is approximately half lipid and half protein. The lipid component consists of phospholipids, free cholesterol, cholesteryl esters, and triglycerides. The protein component includes apo A-I (molecular weight, 28,000 Daltons) and apo A-II (molecular weight, 17,000 Daltons). Other minor but important proteins are apo E and apo C, including apo C-I, apo C-II, and apo C-III.

HDL particles are heterogeneous. They can be classified as a larger, less dense HDL2 or a smaller, more dense HDL3. Normally, most of the plasma HDL is found in HDL3. HDL is composed of 4 apolipoproteins per particle. HDL may be composed of both apo A-I and apo A-TI or of apo A-I only. HDL2 is predominantly apo A-I only, and HDL3 is made of both apo A-I and apo A-TI. HDL particles that are less dense than HDL2 are rich in apo E.

Non-Naturally Occurring Lipoprotein Particles—Engineered Lipoprotein Particles

Accordingly, the present invention provides a series of nanoplatforms with different sizes that can be made from all the lipoproteins, wherein the lipoprotein's core is modified to contain a core particle having (i) an inner part comprising a hydrophilic active agent and a hydrophilic portion of an amphiphilic cholesterol and (ii) an outer part comprising a hydrophobic portion of the amphiphilic cholesterol. In certain embodiments, more than one core particle is encapsulated by the layer comprising phospholipids.

In a preferred embodiment, non-naturally occurring lipoprotein particles are modified lipoprotein particles described in WO 2006/073419 to Zheng et al., wherein the modification comprises substituting the lipophilic core with a core particle having (i) an inner part comprising a hydrophilic active agent and a hydrophilic portion of an amphiphilic cholesterol and (ii) an outer part comprising a hydrophobic portion of the amphiphilic cholesterol.

In other embodiments, the core may further comprise hydrophobic (lipophilic) substances encapsulated together with the core particle(s) by a phopholipid monolayer.

Since each of the apoproteins is targeted to a specific receptor, if receptors are blocked, the lipoproteins can be retargeted to alternate receptors. Moreover, in certain embodiments, both the lipoprotein hydrophobic core and phospholipids monolayer can be modified to carry large payloads of diagnostic and/or therapeutic agents making them exceptional multifunctional nanoplatforms. In certain embodiments, the engineered lipoprotein particles of the present invention contain one or more homing molecules. The engineered lipoprotein particles can also contain a cell death sensor so such engineered lipoprotein particles can simultaneously perform diagnosis, treatment as well as therapeutic response monitoring functions.

The invention provides engineered lipoprotein particles that are based on naturally occurring lipoprotein particles, described above. The term "non-naturally occurring" refers to nanoplatforms that do not exist innately in the human body. Such non-naturally occurring engineered lipoprotein particles can contain one or more components of naturally occurring lipoprotein particles. For example, phopholipids comprising the outer surface of the particle and apoproteins are preferably those which naturally occur.

Additionally, in certain embodiments of the present invention, the naturally occurring cell surface receptors of the lipoprotein particle (e.g., LDL and HDL) are cell surface receptor ligands to the surface of the apoprotein of the naturally occurring lipoprotein particle.

The engineered lipoprotein particles of the present invention are preferably from 5 nm to 500 nm, in diameter, from 5 nm to 100 nm in diameter; and from 5 nm to 80 nm in diameter.

There are several distinct advantages for using lipoprotein based particles for targeted delivery. One advantage of the engineered lipoprotein particles of the present invention is that they are completely compatible with the host immune system, and they are also completely biodegradable. They also provide a recycling system for accumulation of large quantities of diagnostic or therapeutic agents in the target cells. Specifically, being endogenous carriers, lipoprotein particles are not immunogenic and escape recognition by the reticuloendothelial system (RES).

Other advantages include: 1) lipoproteins, which are a physiological carrier, are not cleared by the reticuloendothelial system (RES) and may prolong the serum half-life of drugs/probes by incorporation into it; 2) drug/probe sequestration in the core space provides protection from serum enzyme and water; 3) the availability of the array of lipoproteins provide a series of nanoplatforms with size ranging from 5 nm to 500 nm.

Each lipoprotein particle contains at least one apoprotein that aids in targeting cell surface receptors. For example, LDL contains apoB-100. The mature apoB-100 molecule comprises a single polypeptide chain of 4536 amino acid residues. Chemical modification of functional groups in the apoB-100 molecule has shown that the electrostatic interaction of domains containing basic Lys and Arg residues with acidic domains on the LDLR is important to the binding process. Further examples of apoprotein modifications can be found in WO 2006/073419 to Zheng et al.

The naturally occurring lipoprotein particles each have characteristic apoproteins, and percentages of protein, triacyiglycerol, phospholipids and cholesterol. VLDL particles can contain about 10% protein, about 60% triacyiglycerols, about 18% phopholipids and about 15% cholesterol. LDL particles can contain about 25% protein, about 10% triacylglycerols, about 22% phopholipids and about 45% cholesterol. HDL particles can contain about 50% protein, about 3% triacyiglycerols, about 30% phopholipids and about 18% cholesterol.

Likewise, the phopholipid shell of engineered lipoprotein particles of the invention also contains different percentages of lipids, and may even not contain any percentage of triacyiglycerol.

Homing Molecules

As used herein, the term "home" or "selectively home" means that a particular molecule binds relatively specifically to molecules present in specific organs or tissues following administration to a subject. In general, selective homing is characterized, in part, by detecting at least a two-fold greater selective binding of the molecule to an organ or tissue as compared to a control organ or tissue. In certain embodiments the selective binding is at least three-fold or four-fold greater as compared to a control organ or tissue.

In the case of tumor homing molecules, such molecules bind to receptors that are selectively over-expressed in particular cancer tissues. By over expression is meant at least one and one half greater expression in tumor tissue compared to normal tissue. In certain embodiments, expression is at least five times greater in tumor as compared to non-tumor.

In embodiments of the present invention, a homing molecule is attached to the lipoprotein of the engineered lipoprotein particle of the present invention that targets specific tissues and tumors. A "homing molecule" refers to any material or substance that may promote targeting of tissues and/or receptors in vitro or in vivo with the compositions of the present invention. The targeting moiety may be synthetic, semi-synthetic, or naturally-occurring. The targeting moiety may be a protein, peptide, oligonucleotide, or other organic molecule. The targeting moiety may be an antibody (this term including antibody fragments and single chain antibodies that retain a binding region or hypervariable region).

Materials or substances which may serve as targeting moieties include, but are not limited to, those substances listed in Table 1 below:

TABLE 1

| Targeting Moiety | Target(s) |
| --- | --- |
| Antibodies (and fragments such as Fab, F(ab)'2, Fv, Fc, etc,) | RES system |
| Epidermal growth factor (EGF) | Cellular receptors |
| Collagen | Cellular receptors |
| Gelatin | Cellular receptors |
| Fibrin-binding protein | Fibrin |
| Plasminogen activator | Thrombus |
| Urokinase inhibitor | Invasive cells |
| Somatostatin analogs | Cellular receptors |
| Lectin (WGA) | Axons |
| f-Met-Leu-Phe | Neutrophils |
| Selectin active fragments | Glycosyl structures |
| ELAM, GMP 140 | Leucocyte receptors |
| "RGD" proteins | Integrins, Granulocytes |
| IL-2 | Activated T-cell |
| CD4 | HIV infected cells |
| Cationized albumin | Fibroblasts |
| Carnitine | |
| Acetyl-, maleyl-proteins | Macrophage scavenger receptor |
| Hyaluronic acid | Cellular receptors |
| Lactosylceramide | Hepatocytes |
| Asialofoetuin | Hepatocytes |
| Arabinogalactan | Hepatocytes |
| Galactosylated particles | Kupffer cells |
| Terminal fucose | Kupffer cells |
| Mannose | Kupffer cells, macrophages |
| Lactose | Hepatocytes |
| Dimuramyl-tripeptide | Kupffer cells, macrophages |
| Fucoidin-dextran sulfate | Kupffer cells, macrophages |
| Sulfatides | Brain |
| Glycosyl-steroids | |
| Glycosphyngolipids | Other glycosylated structures |
| Hypoxia mediators | Infarcted tissues |
| Amphetamines | Nervous system |
| Barbiturates | Nervous system |
| Sulfonamides | |
| Monoamine oxidase inhibitor substrates | Brain |
| Chemotactic peptides | Inflammation sites |
| Muscarine and dopamine receptor substrates | Nervous system |

Non-limiting examples of homing molecules include tumor homing molecules which selectively bind to tumor tissue versus normal tissue of the same type. Such molecules in general are ligands for cell surface receptors that are overexpressed in tumor tissue. Cell surface receptors over-expressed in cancer tissue versus normal tissue include, but are not limited to, epidermal growth factor receptor (EGFR) overexpressed in anaplastic thyroid cancer and breast and lung tumors, metastin receptor overexpressed in papillary thyroid cancer, ErbB family receptor tyrosine kinases overexpressed in a significant subset of breast cancers, human epidemal growth factor receptor-2 (Her2/neu) overexpressed in breast cancers, tyrosine kinase-18-receptor (c-Kit) overexpressed in sarcomatoid renal carcinomas, HGF receptor c-Met overexpressed in esophageal adenocarcinoma, CXCR4 and CCR7 overexpressed in breast cancer, endothelin-A receptor overexpressed in prostate cancer, peroxisome proliferator activated receptor delta (PPAR-delta) overexpressed in most colorectal cancer tumors, PDGFR A overexpressed in ovarian carcinomas, BAG-i overexpressed in various lung cancers, soluble type II TGF beta receptor overexpressed in pancreatic cancer folate and integrin (e.g. aV 133). The folate receptor is a glycosyiphosphatidylinositol-anchored glycoprotein with high affinity for the vitamin folic acid. Folate receptor has been identified as a tumor-marker, which is expressed at elevated levels relative to normal tissues on epithelial malignancies, such as ovarian, colorectal, and breast cancer.

Other types of homing molecules include tumor homing molecules and organ and tissue homing molecules as described in paragraphs [0066]-[0077] of WO 2006/073419 to Zheng et al.

Active Agents

A variety of active agents can be delivered via the engineered lipoprotein particles of the present invention in addition to the hydrophilic active agent. In embodiments, the lipophilic active agent substances are encapsulated by a phopholipid monolayer together with the amphiphilic cholesterol coated and encapsulated hydrophilic active agent.

The term "lipophilic compound" or "lipophilic drug" is defined as a compound or drug which in its non-ionized form is more soluble in lipid or fat than in water. Examples of lipophilic compounds include, but are not limited to, acetanilides, anilides, aminoquinolines, benzhydryl compounds, benzodiazepines, benzofurans, carinabinoids, cyclic peptides, dibenzazepines, digitalis gylcosides, ergot alkaloids, flavonoids, imidazoles, quinolines, macrolides, naphthalenes, opiates (or morphinans), oxazines, oxazoles, phenylalkylamines, piperidines, polycyclic aromatic hydrocarbons, pyrrolidines, pyrrolidinones, stilbenes, sulfonylureas, sulfones, triazoles, tropanes, and ymca alkaloids.

A variety of tests can be used to determine lipophilicity. A common test protocol is measurement of the octanol-water partition coefficient ($P_{ow}$, $K_o$), which is a measure of lipophilicity by determination of the equilibrium distribution between octan-1-ol and water. Lipophilic drugs are those drugs that preferably partition into the octanol component.

Pharmaceutically active lipophilic drugs which may be incorporated into targeted drug delivery complexes of the invention include drugs for the treatment of cancer and glaucoma, immunoactive agents, antineoplastic agents, anticholinergic and cholinomimetic agents, antimuscarinic and muscarinic agents, antiadrenergic and antiarrhythmics, antihypertensive agents, anti-inflammatory drugs, antibiotic drugs, anti-fungal drugs, steroids, anti-histamines, anti-asthmatics, sedatives, anti-epileptics, anesthetics, hypnotics, antipsychotic agents, neuroleptic agents, antidepressants, anxiolytics, anti-convulsant agents, neuron blocking agents, narcotic antagonists, analgesics, anti-proliferative agents, anti-viral drugs, hormones, and nutrients.

Examples of anti-cancer drugs include but are not limited to paclitaxel, docosahexaenoic acid (DHA)-paclitaxel conjugates, cyclophosphoramide, betulinic acid, and doxorubicin (see, e.g. U.S. Pat. No. 6,197,809 to Strelchenok).

Examples of anti-glaucoma drugs include but are not limited to n-blockers such as timolol-base, betaxolol, atenolol, livobunolol, epinephrine, dipivalyl, oxonolol, acetazolamide-base and methzolamide.

Examples of anti-inflammatory drugs include but are not limited to steroidal drugs such as cortisone and dexamethasone and non-steroidal anti-inflammatory drugs (NSAID) such as piroxicam, indomethacin, naproxen, phenylbutazone, ibuprofen and diclofenac acid. Examples of anti-asthmatics include but are not limited to prednisolone and prednisone. (See also U.S. Pat. No. 6,057,347).

An example of an antibiotic drug includes but is not limited to chloramphenicol. Examples of anti-lungal drugs include but are not limited to nystatin, amphotericin B, and miconazole. Examples of an anti-viral drug includes but is not limited to Acyclovir™ (Glaxo Wellcome, U. K.).

Examples of steroids include but are not limited to testosterone, estrogen, and progesterone. Examples of anti-allergic drugs include but are not limited to pheniramide derivatives. Examples of sedatives include but are not limited to diazepam and propofol.

Nucleic acids (generally hydrophilic) may be delivered in the core particle by mixing them with the hydrophilic active agent prior to contacting with amphiphilic cholecterol.

Hydrophilic Agents with Lipid Anchors

In addition to active agents that are hydrophilic and can be loaded into the core of the engineered lipoprotein particles of the present invention, the invention also includes agents that can be loaded onto the surface of the apoproteins of the present invention. Such agents can be hydrophilic with a lipid anchor. For example, the engineered lipoprotein particles of the present invention can be modified to include a lipophilic chelator, such lipophilic chelators are well known in the art. For example, the lipophilic chelator, DTPA Bis(stearylamine), can be incorporated into an LDL particle using standard techniques. Likewise 1,1-dioctadecyl-3,3,3,3-tetramethylindocarbocyanine perchlorate (Dii), be used as a lipid-anchored, carbocanine based optical probe known to intercolate into the LDL phospholipid monolayer and can be used in the LBNPs of the present invention.

Similarly, near infrared ("NIR") probes such as tricarbocyanine dyes, which are NIR fluorophores, can be modified to include a lipid-chelating anchor that allows such probes to be anchored to the engineered lipoprotein particles of the present invention. Any such lipid-chelating anchors can be used, for example, a cholesteryl laurate moiety can be attached to the NIR probes to anchor them to the engineered lipoprotein particles of the present invention. (Zheng et al., Bioorg. & Med. Chem Lett. 12:1485-1488 (2002). Diagnostic Agents other than MRI Contrast Agents In one embodiment, an active agent can be a detectable agent such as a radionuclide or an imaging agent, which allows detection or visualization of the selected organ or tissue depending on the type of homing molecule associated with a particular engineered lipoprotein particle (e.g., a lung, skin, pancreas, retina, prostate, ovary, lymph node, adrenal gland, liver or gut homing molecule). The type of detectable agent selected will depend upon the application. For example, for an in vivo diagnostic imaging study of the lung in a subject, a lung homing molecule can be linked to an engineered lipoprotein particle comprising an agent that, upon administration to the subject, is detectable external to the subject. For detection of such internal organs or tissues, for example, the prostate, a gamma ray emitting radionuclide such as indium-113, indium-115 or technetium-99 can be conjugated with an engineered lipoprotein particle that is linked to a prostate homing molecule and, following administration to a subject, can be visualized using a solid scintillation detector. Alternatively, for organs or tissues at or near the external surface of a subject, for example, retina, a fluorescein-labeled retina homing molecule can be used such that the endothelial structure of the retina can be visualized using an opthalamoscope and the appropriate optical system.

Molecules that selectively home to a pathological lesion in an organ or tissue similarly can be used in the engineered lipoprotein particle of the invention to deliver an appropriate detectable agent such that the size and distribution of the lesion can be visualized. For example, where an organ or tissue homing molecule homes to a normal organ or tissue, but not to a pathological lesion in the organ or tissue, the presence of the pathological lesion can be detected by identifying an abnormal or atypical image of the organ or tissue, for example, the absence of the detectable agent in the region of the lesion.

A detectable agent also can be an agent that facilitates detection in vitro. For example, an engineered lipoprotein particle conjugate comprising a homing molecule and an enzyme, which produces a visible signal when an appropriate substrate is present, can detect the presence of an organ or tissue to which the homing molecule is directed. Such a conjugate, which can comprise, for example, alkaline phosphatase or luciferase or the like, can be useful in a method such as immunohistochemistry. Such a conjugate also can be used to detect the presence of a target molecule, to which the organ homing molecule binds, in a sample, for example, during purification of the target molecule.

Additional diagnostic agents include contrast agents other than MRI contrast agents, radioactive labels and fluorescent labels, optical contrast agents, ultrasound contrast agents, X-ray contrast agents and radio-nuclides.

Therapeutic Agents

A therapeutic agent can be any biologically useful agent that exerts its function at the site of the selected organ or tissue. For example, a therapeutic agent can be a small organic molecule that, upon binding to a target cell due to the linked organ homing molecule, is internalized by the cell where it can affect its function. A therapeutic agent can be a nucleic acid molecule that encodes a protein involved in stimulating or inhibiting cell survival, cell proliferation or cell death, as desired, in the selected organ or tissue. For example, a nucleic acid molecule encoding a protein such as Bcl-2, which inhibits apoptosis, can be used to promote cell survival, whereas a nucleic acid molecule encoding a protein such as Bax, which stimulates apoptosis, can be used to promote cell death of a target cell.

A particularly useful therapeutic agent that stimulates cell death is ricin, which, when linked to an organ homing molecule of the invention, can be useful for treating a hyperproliferative disorder, for example, cancer. An engineered lipoprotein particle comprising an organ homing molecule of the invention and an antibiotic, such as ampicillin or an antiviral agent such as ribavirin, for example, can be useful for treating a bacterial or viral infection in a selected organ or tissue.

A therapeutic agent also can inhibit or promote the production or activity of a biological molecule, the expression or deficiency of which is associated with the pathology. Thus, a protease inhibitor can be a therapeutic agent that, when linked to an organ homing molecule, can inhibit protease activity at the selected organ or tissue, for example, the pancreas. A gene or functional equivalent thereof such as a cDNA, which can replenish or restore production of a protein in a selected organ or tissue, also can be a therapeutic agent useful for ameliorating the severity of a pathology. A therapeutic agent also can be an antisense nucleic acid molecule, the expression of which inhibits production of a deleterious protein, or can be a nucleic acid molecule encoding a dominant negative protein or a fragment thereof, which can inhibit the activity of a deleterious protein.

Pharmaceutical Compositions

When administered to a subject, the engineered lipoprotein particles of the present invention are administered as a pharmaceutical composition containing, for example, the conjugate and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of the complex. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. The pharmaceutical composition also can contain an agent such as a cancer therapeutic agent or other therapeutic agent as desired.

As noted above, the engineered lipoprotein particles of the present invention may be provided in a physiologically or pharmaceutically acceptable carrier, or may be provided in a lyophilized form for subsequent use. The compositions are optionally sterile when intended for parenteral administration or the like, but need not always be sterile when intended for some topical application. Any pharmaceutically acceptable carrier may be used, including but not limited to aqueous carriers. Aqueous carriers for parenteral injections include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

One skilled in the art would know that a pharmaceutical composition containing the engineered lipoprotein particles of the present invention can be administered to a subject by various routes including, for example, orally or parenterally, such as intravenously. The composition can be administered by injection or by intubation.

In performing a diagnostic or therapeutic method as disclosed herein, a therapeutically effective amount of the engineered lipoprotein particles of the present invention must be administered to the subject. A "therapeutically effective amount" is the amount of the conjugate that produces a desired effect. An effective amount will depend, for example, on the active agent and on the intended use. For example, a lesser amount of a radiolabeled conjugate can be required for imaging as compared to the amount of the radiolabeled molecule administered for therapeutic purposes, where cell killing is desired. A therapeutically effective amount of a particular conjugate for a specific purpose can be determined using methods well known to those in the art.

In principle, an organ homing molecule as part of the engineered lipoprotein particle of the present invention of the invention can have an inherent biological property, such that administration of the molecule provides direct biological effect. For example, an organ homing molecule can be sufficiently similar to a naturally occurring ligand for the target molecule that the organ homing molecule mimics the activity of the natural ligand. Such an organ homing molecule can be useful as a therapeutic agent having the activity of the natural ligand. For example, where the organ homing molecule mimics the activity of a growth factor that binds a receptor expressed by the selected organ or tissue, such as a skin homing molecule that mimics the activity of epidermal growth factor, administration of the organ homing molecule can result in cell proliferation in the organ or tissue. Such inherent biological activity of an organ homing molecule of the invention can be identified by contacting the cells of the selected organ or tissue with the homing molecule and examining the cells for evidence of a biological effect, for example, cell proliferation or, where the inherent activity is a toxic effect, cell death.

Methods of making engineered lipoprotein particles of the invention differ from methods described in WO 2006/073419 to Zheng et al. by methods of making a core. In one embodiment, the core is made by an emulsion route. In another embodiment, the core is made via a high temperature treatment. Depending on the desired method, the MRI contrast agent is dissolved in an aqueous or organic solution. By adding a base (for the emulsion route) or via high temperature treatment (for the organic route) in the presence of the amphiphilic cholesterol, the core or cholesterol-coated MRI contrast agent particles are obtained. Inventors have discovered that by using the amphiphilic cholesterol as a starting cholesterol material (i.e., containing a polar head and a lipophilic tail (e.g., cholic acid)), the polar group is then naturally incorporated to the surface of the core, and the remaining body of cholesterol, with its lipophilic tail, is repelled from the core's inner surface and is exposed to the oily surrounding. Advantageously, this allows suspending the core or cholesterol-coated MRI contrast agent particles in the (oily) solution. Thus, the cholesterol-coated MRI contrast agent particle suspension is essentially indistinguishable from a cholesterol suspension and may therefore be used for further lipoprotein formation in the same way as cholesterol.

In the embodiment which uses high temperature, smaller, cholesterol-coated MRI contrast particles can be obtained. Preferably, the cholesterol-coated MRI contrast agent particles are cholesterol-coated iron oxide particles. The embodiment that uses the emulsion method does not involve high temperatures and is suitable for incorporating substances that are heat sensitive, such as proteins that are intended for therapeutic substance.

The methods of the invention offer several advantages. First, the hydrophilic active agent (e.g., MRI contrast agent) containing particles are formed homogeneously and always have a coating of cholesterol. Second, after formation, the free cholesterol can be completely removed, so any further reaction involving cholesterol fully incorporates iron oxides in the core. Thus, the formation of lipoprotein that contains only cholesterol and not MRI contrast agent/therapeutic substance is avoided. Third, the size of the cholesterol-coated MRI contrast agent/therapeutic substance particles can be controlled, for example, by using various preparation and separation schemes, to tune up the properties of the engineered lipoprotein. Four, the content of the MRI contrast agent in the cholesterol-like substance is very high, so the pay-load in the engineered lipoprotein is also high.

The High Temperature Method of Making the Core

The high temperature method of making the core includes the following steps providing a hydrophilic active agent source, providing an organic solvent, providing a hydrophobic diol, providing an amphiphilic cholesterol, combining the hydrophilic active agent source, the organic solvent, the hydrophobic diol, and the amphiphilic cholesterol under an inert gas to form a mixture, and heating the mixture to a temperature of about 180° C. to about 375° C. during a time interval sufficient to form the core particle.

In certain embodiments, amphiphilic cholesterol is a steroid acid. Preferably, the steroid acid is at least one of cholic acid, deoxycholic acid, chenodeoxylcholic acid, taurocholic acid, or clycocholic acid.

Hydrophilic Active Agent Source

A source of a hydrophilic active agent or a precursor of a hydrophilic active agent of the invention is a substance which is subjected to a chemical change prior to becoming a hydrophilic active agent.

In certain embodiments of the method, the hydrophilic active agent source is an MRI agent source. The MRI agent source comprises a compound having a metal group selected from Fe, Co, Mn, Ni, and Cr, organometallic iron precursor such as iron acetoacetonate, iron pentacarbonyl, iron dodecarbonyl, iron ethoxide, and iron iso-propoxide. Fe(III), Co, and Mn are most preferred. The MRI agent source needs to be hydrophobic if the high temperature method is used. The high temperature process occurs in the presence of an oily environment, but the product contains a part (iron oxide) that is hydrophilic and wrapped inside the amphiphilic cholesterol. This differs from the emulsion method where the MRI agent source (precursor) is hydrophilic. After reaction, the source precursor is turned into the MRI agent, for example, iron oxide, which is hydrophilic.

In certain embodiments of the high temperature method, the organic solvent is at least one of ethers or alkanes. In certain embodiments, the organic solvent is at least one of phenyl ether, dioctylether, or octadecane.

Organic solvents can be used to control, among other things, the boiling temperature, hence the particle size. (Please note these are all hydrophobic.)

In certain embodiments of the high temperature method, the hydrophobic diol is at least one of hexadecanediol, docecanediol or tetradecanediol. Diol is a reducing agent of organometallic iron precursor. Without being bound to a particular theory, the possible role of diol is to initiate or catalyze the reaction.

Advantageously, the inventors have discovered that using high temperatures did not cause oxidation of cholesterol and the obtained core particle was sufficiently similar to the cholesterol core containing no other inclusions.

In a preferred embodiment, the core particle made by the high temperature method as described above has a diameter of about 5 to about 200 nanometers.

The Emulsion Method of Making the Core

The emulsion method of making the core of the invention includes the following steps: providing a first water phase comprising a hydrophilic active agent source; providing a first oil phase comprising an amphiphilic cholesterol which is a cholesterol-based surfactant; combining the water phase and the oil phase to form a first water-in-oil emulsion; providing a second water phase comprising an OH-source; providing a second oil phase comprising a cholesterol-based surfactant; combining the second water phase and the second oil phase to form a second water-in-oil emulsion; combining the first water-in-oil emulsion with the second water-in-oil emulsion, and thereby forming the core particle.

In certain embodiments of the method, the MRI agent source is selected from water soluble salts of Fe, Co, Mn, Ni, and Cr. An MRI agent source in the "water" phase include, for example, iron chloride, iron nitrate, iron sulfate, and iron acetate. Any soluble metal salt that is hydrophilic can be used. The MRI agent source is introduced as the water phase in a water-in-oil emulsion.

In certain embodiments of the method, the amphiphilic cholesterol-based surfactant is at least one of the cholesteryl 3β-N-(dimethylaminoethyl)carbamate hydrochloride, sodium cholesteryl sulfate, or cholesterol-PEG. The cholesterol-based surfactant is in the "oil" phase. In order to act as a surfactant (one end to be attached to iron oxide, the other end for suspension in the oil phase), it should be a cholesterol that contains some polar head, such as, for example, cholesteryl 3β-N-(dimethylaminoethyl)carbamate hydrochloride, sodium cholesteryl sulfate, cholesterol-PEG.

Non-limiting examples of the OH-source are ammonium hydroxide and sodium hydroxide. The preferred way is to introduce the OH-source by way of the water phase in another water-in-oil emulsion, which is added to the emulsion of 1 and 2. In one embodiment, $NH_4OH$ is used but other OH-sources can also be used; the OH-source is chosen to control the rate of reaction.

Also provided is a core particle made by the emulsion method as described above, wherein the core has a diameter of a diameter of about 5 to about 1000 nanometers.

The inventors have discovered that unlike the previously known methods utilizing water-soluble coatings or surfactants to achieve precipitation and trapping of iron oxide particles, using an oily coating allows to obtain the cholesterol-like core having the inner surface comprising desired MRI contrast agent/therapeutic substance particles. Thus, contrary to the accepted wisdom to trap hydrophobic substances, in the current invention, the hydrophilic substances are trapped. The trapped hydrophilic substance in an oily coating can in turn be used to constitute the core of lipoproteins, which are transported in the body fluid.

Non-limiting examples of an "oil" phase are chloroform, methylene chloride, and hexane. In one embodiment, chloroform is used. An oil phase that has high vapor pressure and can be completely evaporated is preferred.

Non-limiting examples of a "water" phase are $H_2O$ or other substance, as long as it can be used to introduce the desired metal salt, and possibly, the OH source, e.g., an alcohol-water mixture.

In the case of hydrophilic therapeutic substance is to be incorporated directly inside the cholesterol shell, the substance can be included, in the emulsion method, in the water portion of the water/oil emulsion, and the cholesterol in the oil portion of the water/oil emulsion. If additional reaction involving two hydrophilic substances is desired, then each of the two reactants can be incorporated, separately, in the water portion of one emulsion, and the two emulsions containing two water portions that incorporates two reactants will be mixed, so that reactions between the water portions will occur in the presence of cholesterol that is in the oil portion of the emulsion.

The Method of Making the Engineered Lipoprotein

The method of making the engineered lipoprotein includes the following steps: providing the cholesterol coated core particle as described above, adding a phospholipid to the core particle or the plurality of core particles to form a phospholipid layer surrounding the core particle or the plurality of core particles and thereby forming a phospholipids micelle; and adding an apoprotein to the phospholipids micelle and thereby making the engineered lipoprotein.

In certain embodiments, the method of making an engineered lipoprotein further comprises adding a homing molecule.

In certain embodiments, the method of making an engineered lipoprotein further comprises adding a hydrophobic active agent to the core particle or the plurality of particles prior to adding the phospholipid and forming the phospholipid layer surrounding a mixture of the core particle or the plurality of core particles and the hydrophobic active agent.

A non-limiting example of conjugating a guest molecule to the engineered lipoprotein is demonstrated using FITC as a homing molecule.

In the case a hydrophobic therapeutic substance is to be incorporated into the micelle, the substance can be added to the core at the same time a phospholipid is added. The solution is dispersed in an oily solution of high vapor pressure, which can then be dried to leave an intimately mixed substance of the core, the therapeutic substance, and phospholipid. After adding water to this mixture, a phospholipid micelle is formed that incorporates the core and the therapeutic substance.

Pharmaceutical compositions associated with the engineered lipoprotein of the invention as described above can be monitored by known imaging or diagnostic techniques, e.g., by tracking MRI contrast agents associated with the engineered lipoprotein particles.

Thus, the invention provides is a method of using the engineered lipoprotein of the invention, the method comprising administering the engineered lipoprotein to the cell or the tissue and thereby causing the engineered lipoprotein to bind to a selected receptor on the cell or the tissue, and monitoring the engineered lipoprotein position in a cell by recording a signal detectable by MRI.

A person skilled in the art would understand that any appropriate molecule which can bond with the surface of the engineered lipoprotein is contemplated in this invention.

The invention will be illustrated in more detail with reference to the following Examples, but it should be understood that the present invention is not deemed to be limited thereto.

EXAMPLES

Example 1

Figure 1B:
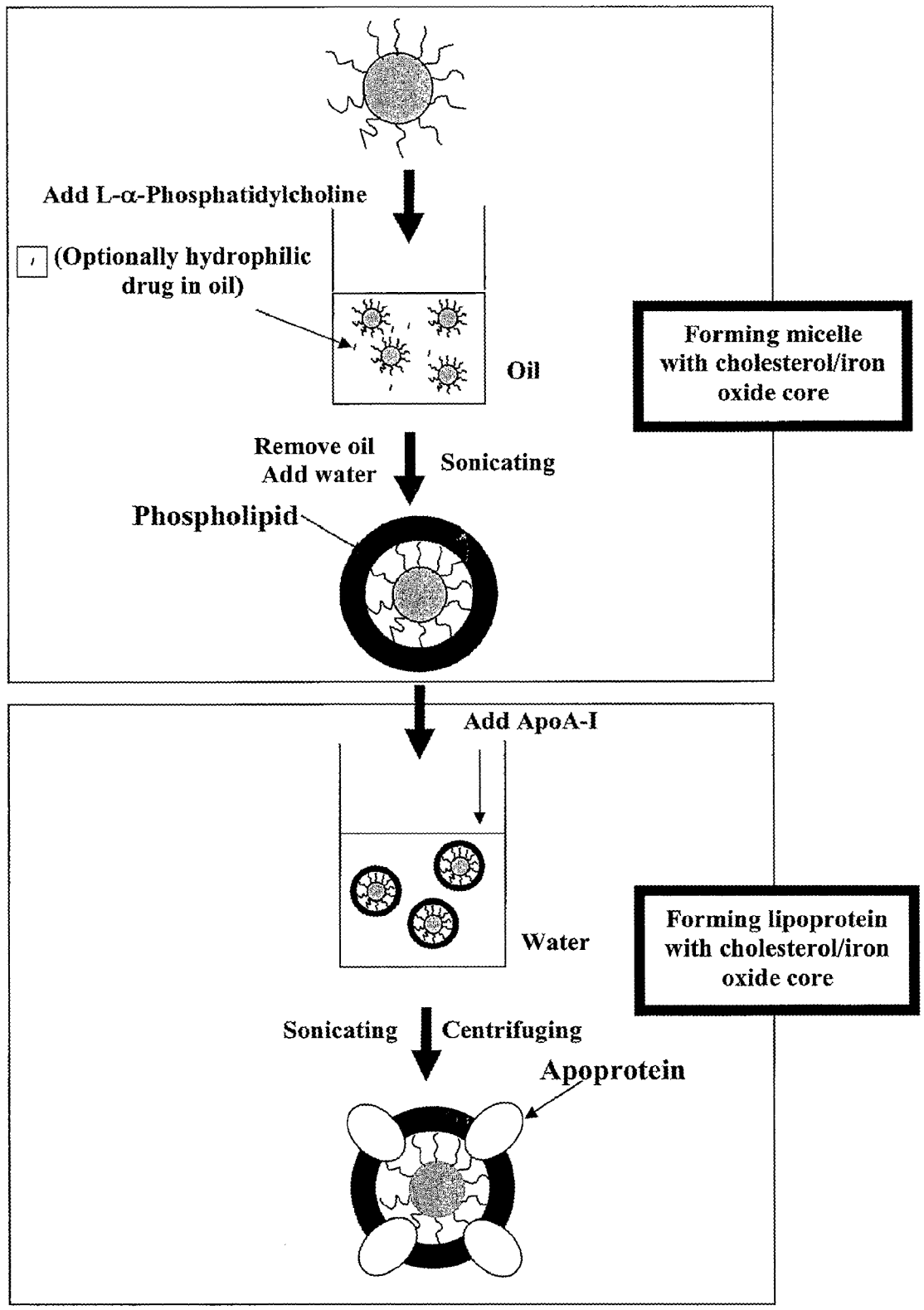
Figure 2A:
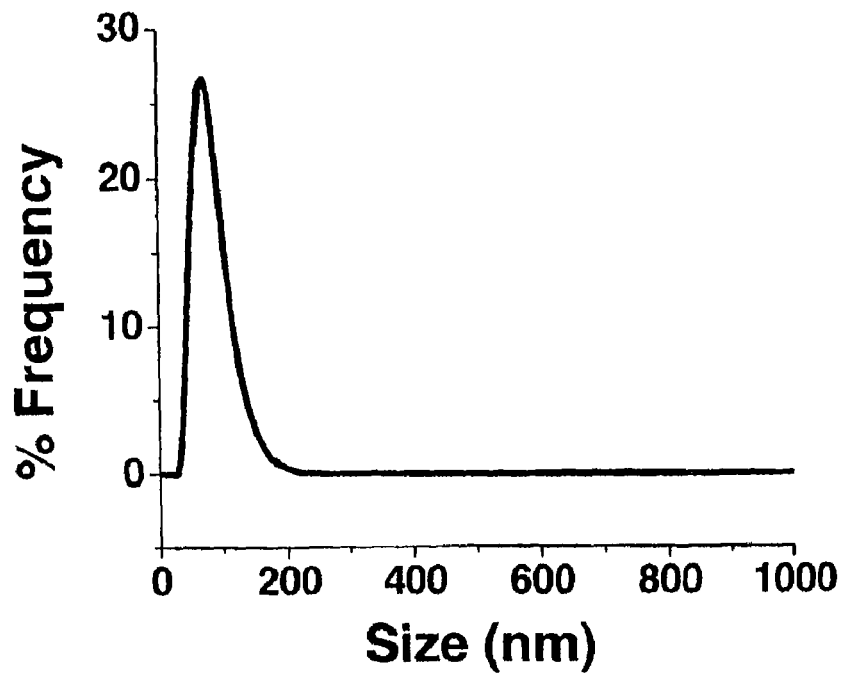
FIG. 2A is a graph demonstrating a size distribution of cholesterol-coated iron oxide.
Figure 2B:
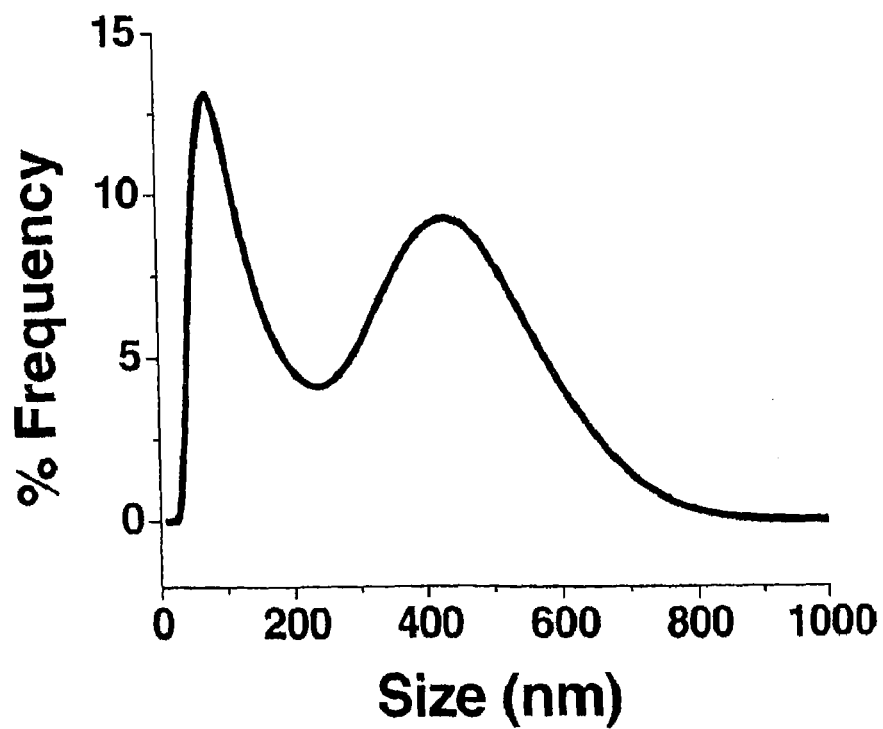
FIG. 2B is a graph demonstrating a size distribution of lipoproteins with iron oxide core. The secondary peak is due to agglomeration of lipoproteins.
Figure 3:
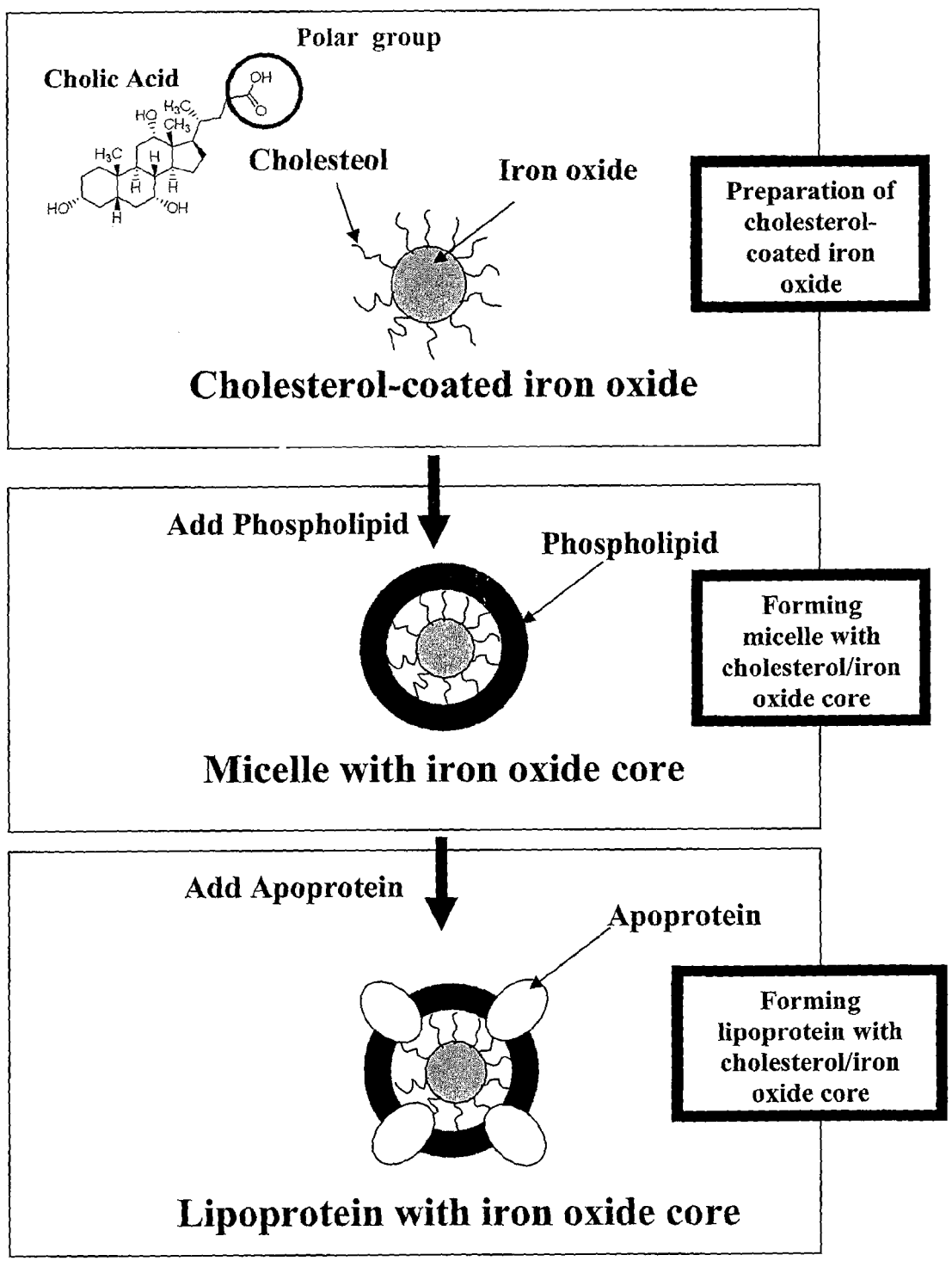
FIG. 3 is a scheme demonstrating one embodiments of the method of the invention, wherein a reconstituted lipoprotein with a cholesterol coated iron oxide core is made and wherein the coated core was obtained by reacting iron oxide and cholic acid at high temperature.
Figure 4A:
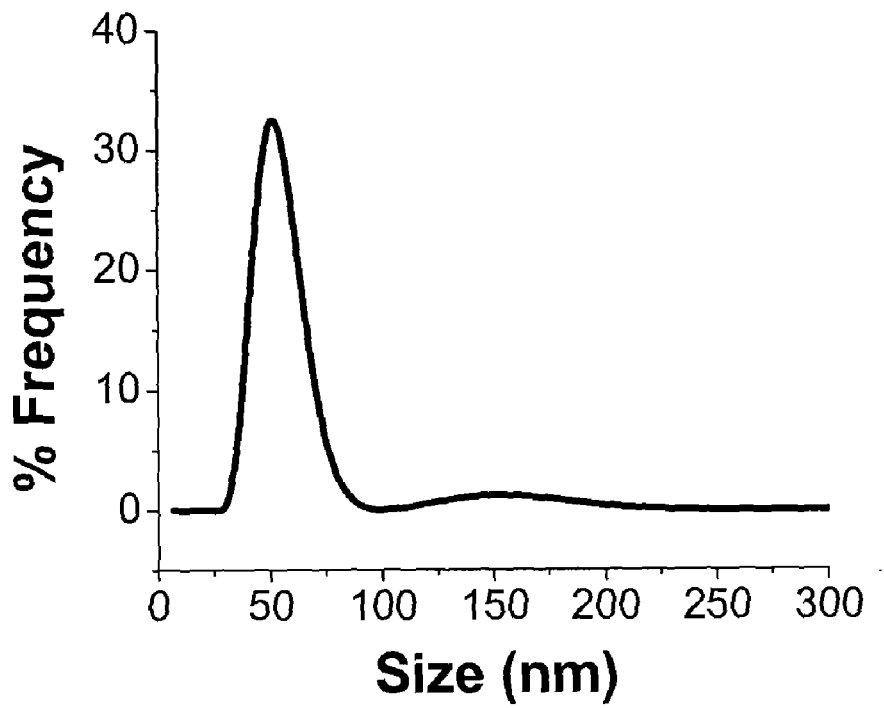
FIG. 4A is a graph demonstrating a size distribution of micelle containing a cholesterol coated iron oxide in a phospholipid shell.
Figure 4B:
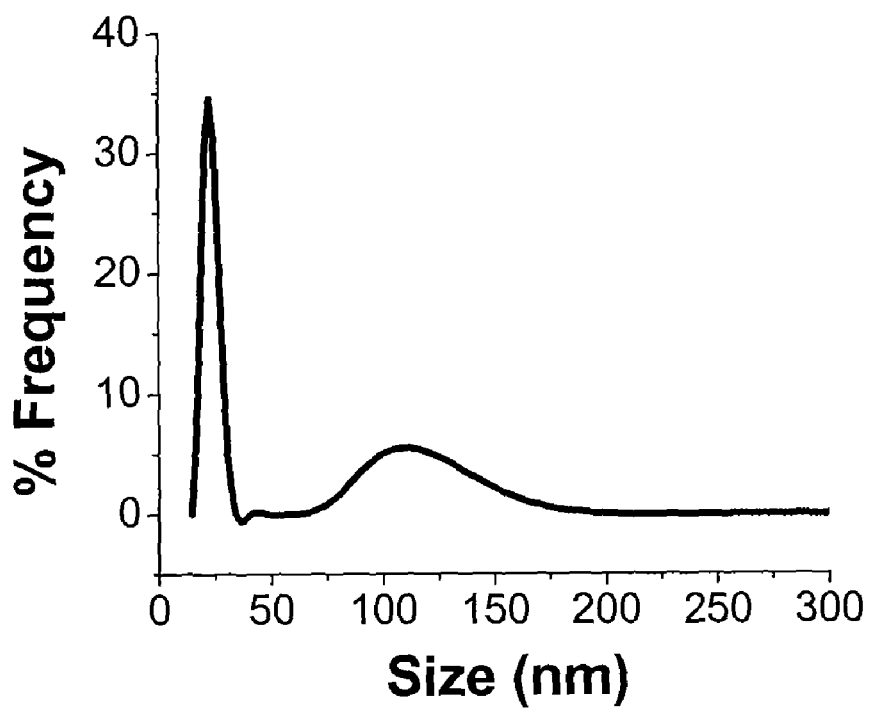
FIG. 4B is a graph demonstrating a size distribution of lipoproteins containing a cholesterol coated iron oxide core. The primary particle size decreases from FIG. 4A to FIG. 4B Secondary peak in FIG. 4B is due to agglomeration of lipoproteins.

The Emulsion Process of Making the Core and the Engineered Lipoprotein (See FIGS. 1A-1B)

One preferred procedure is illustrated below using the example of a water/oil (W/O) emulsion. Two water phases are separately prepared. One contains iron precursors, the other contains $NH_4OH$. To form W/O emulsions they are separately added to an oil phase that also contains cholesterol. The cholesterol is cholesteryl 3β-N-(dimethylaminoethyl) carbamate hydrochloride which has a polar head of dimethyl amine. This polar-head-containing cholesterol serves as a surfactant aiding formation of emulsion of water-phase droplets in the oil phase. Sonication is used in the above procedure to aid emulsion formation. The two emulsions are then combined and mixed to allow reactions between iron precursors and $OH^-$, causing iron oxide precipitation. The iron oxide precipitate, in the meantime, is coated by the polar head of the cholesterol from the surrounding oil phase, so it remains in the solution. This experiment demonstrates that the iron oxide is already coated by cholesterol, because otherwise it can not be suspended in the oil phase. The reacted emulsion is then dried. A new portion of chloroform is added again. Using centrifugation, the reacted cholesterol-coated iron oxide particles are collected and the remaining oily phase that contains un-reacted free cholesterol is discarded. The cholesterol-coated iron oxide is resuspended in the oily phase, and a phospholipid is added to the colloid. The solution is dried, then a water phase is added and the new solution is sonicated to form an (O/W) lipid micelle that contain a shell of phospholipid and a core of cholesterol-coated iron oxide particle(s). Lastly, apoprotein is added and the suspension sonicated to form lipoprotein particles, which are lipid micellae decorated by apoproteins. The final product of lipoprotein particles are separated by centrifugation after discarding the supernatant that contains free apoprotein and phospholipid.

The size of the product was determined at various stages of formation. The size of emulsion droplets in the two initial water phases was bimodal, centered at about 250-300 nm and 750-800 nm. The size of cholesterol-coated iron oxide particles was also initially bimodal, but after centrifugation to remove the large particles a single size around 75 nm was obtained. This indicates that the iron oxide precipitates from the larger droplets in the initial W/O emulsion were excluded from the final product. The phospholipid micellae are initially comprised of three size groups. After centrifugation to remove the largest one, two remaining sizes for particles were still observed. The first size was similar to that of cholesterol-coated iron oxide and may be identified as a lipoprotein that contains a single set of cholesterol-coated colloid. The second size was larger and is due to the aggregation of such iron oxide colloid and/or lipoprotein particles during lipoprotein formation and separation.

To ascertain that the lipoprotein contains apoprotein, FITC was used to conjugate to the amine group of apoprotein located on the surface of the lipoprotein. The resulting "labeled" lipoprotein was found to be fluorescently green confirming that it indeed contained apoprotein.

The primary particle size of iron oxide prepared by reaction of Fe chloride precursors and $OH^-$ is typically around 6-11 nm. Therefore, the size of 75 nm of cholesterol coated iron oxide is a reflection of the aggregates of small iron oxide particles and the size of the coating.

Other variations of the above method can be used. These include: organic iron precursors to prepare cholesterol-coated iron oxide particles, and other forms of cholesterol and apoproteins. Specially, small particles below 20 nm may be prepared by decomposition of organic precursors, using a procedure that is similar to the one described above after replacing oleic acid and oleylamine by an appropriate cholesterol that contains a polar head group. (See Example 3, Hydrophobic iron oxide particles).

Example 2

The High Temperature Process of Making the Core and the Engineered Lipoprotein

This example illustrates the high temperature process of making the core comprising iron oxides that are as small as 3-5 nm and a cholesterol coating. These cholesterol-coated iron oxide particles are then packaged in a similar way as above to form the engineered lipoprotein. Iron(III) acetylacetonate (2 mmol) was added to phenyl ether (20 ml) with 1,2-hexadecanediol (10 mmol) and cholic acid (12 mmol) under nitrogen. (In the above, cholic acid is the source of cholesterol.) The solution was then heated in nitrogen to 265° C. for 30 min to form iron oxide particles that are cholesterol coated. The mixture was treated with ethanol under air to collect oily particles. The cholesterol-iron oxide was separated by centrifugation at 20,000 rpm. The separated iron oxide particles were dispersed and suspended in (oily phase) chloroform.

To form micellae, 300 µl of egg yolk phosphatidylcholine (20 mg/ml) was added as surfactant to 100 µl of the above cholesterol-coated iron oxide (chloroform) suspension and the solution were dried in nitrogen. A phosphate buffer solution (PBS) including 1 mM EDTA and 0.025% $NaN_3$ was added as water phase to the dried sample and sonicated for 30 min at 50° C. to form O/W phospholipid micelle containing a shell of phospholipid and a core of cholesterol-coated iron oxide particle(s).

To form the engineered lipoprotein, 0.6 mg of apoprotein A-I was added gradually to 5 ml of the above solution under sonication. Sonication continued for 30 min at 40° C. after all apoprotein had been added to allow apoprotein to decorate phospholipid micellae, forming lipoprotein particles. Finally, iron oxide-containing lipoprotein particles with a total size of 20 nm were obtained after filtering using 0.1 μl filter. The final size of iron-oxide-containing engineered lipoprotein was about 20 nm.

Example 3

Hydrophobic Iron Oxide Particles-Comparative Example

Iron(III) acetylacetonate (2 mmol) was added to phenyl ether (20 ml) with 1,2-hexadecanediol (10 mmol), oleic acid (6 mmol) and oleylamine (6 mmol) under nitrogen. The solution was then heated in nitrogen to 265° C. for 30 min. The mixture was treated with ethanol under air to collect oily particles. The separated iron oxide particles were dissolved in hexane for further use.

Iron oxide particles of 8.9 nm in size were obtained. These particles were then used in making lipoprotein by a different protocol from that described above. This protocol involves mixing an oily phase and a water phase in the presence of a phospholipid surfactant, so once the hydrophobic iron oxide particles is suspended in the oily phase, it can be incorporated with the rest of the oily content (such as cholesterol). This procedure was not successful arguably due to the phase separation, during (oily) solvent evaporation, between the hydrophobic iron oxide particles and the cholesterol, both in the oily phase. As a result, the phospholipid micelle formed typically contained only cholesterol and no iron oxide. In addition, even if some such micelle contained iron oxide, it was difficult to separate them from the ones that did not. Lastly, the iron oxide content in the small micelle was statistically low, because the volume fraction of iron oxide was by necessity much smaller than that of cholesterol and the remaining oily phase.

Example 3 demonstrates that without the emulsion process or the high temperature process, it is very difficult to make the cholesterol-coated-iron-oxide core.

Example 4

Cholesterol-Coated Iron Oxide Particles a (the Emulsion Method Performed at Low Temperature)

Two water-phase solutions, one containing an iron precursor in water, the other a base solution of $H_2O$ with 10% $NH_4OH$, were prepared. The water-phase solution with an iron precursor contained a mixture solution of $FeCl_3.6H_2O$ (0.75 g) and $FeCl_2.4H_2O$ (0.32 g) in 10 ml of water. Then, 20 μl of each of the above "water phase" solutions was added to 2 cc of the "oil phase", which is chloroform containing 0.2% Cholesteryl 3β-N-(dimethylaminoethyl)carbamate hydrochloride. Both mixtures were separately sonicated to obtain emulsions. The two emulsions were then mixed together, and dried in nitrogen for 1 hr. After that, chloroform was added again to re-suspend the emulsion. Large particles were then removed by centrifugation at 5,000 rpm for 20 min. The supernatant was again centrifuged at 7,000 rpm for 30 min to collect particles, whereas the supernatant that contained free cholesterol was discarded. The collected particles were re-suspended in chloroform to obtain a suspension of oily dark-brown cholesterol-coated iron oxide particles.

Example 5

Cholesterol-Coated Iron Oxide Particles (the Method Performed at High Temperature)

Iron(III) acetylacetonate (2 mmol) was added to phenyl ether (20 ml) with 1,2-hexadecanediol (10 mmol) and cholic acid (12 mmol) under nitrogen. The solution was then heated in nitrogen to 265° C. for 30 min. The mixture was treated with ethanol under air to collect oily particles. The cholesterol-iron oxide was separated by centrifugation at 20,000 rpm. This method results in cholesterol-coated iron oxide particles which have a core size as small as 3-5 nm.

Example 6

Formation of Phospholipid Micellae

100 μl of egg yolk phosphatidylcholine (20 mg/ml) was added to 2 ml of the above cholesterol-coated iron oxide (chloroform) suspension and the solution was dried in nitrogen. A phosphate buffer solution (PBS) including 1 mM EDTA and 0.025% $NaN_3$ was added to the dried sample and sonicated for 30 min at 50° C. to form phospholipid micellae containing a shell of phospholipid and a core of cholesterol-coated iron oxide particle(s).

Example 7

Formation of Lipoprotein 0.2 mg of apoprotein A-I in 2.5M urea was added gradually to 1 ml of the above liposome-containing PBS solution under sonication. Sonication continued for 10 min at 40° C. after all apoprotein had been added to allow apoprotein to decorate phospholipid micelle, forming lipoprotein particles. After separation of free apoprotein and phospholipid using centrifugation at 7,000 rpm for 20 min, lipoprotein particles/composites were obtained by centrifugation at 7,000 rpm for 20 min, after discarding the supernatant that contained free apoprotein and phospholipid.

Example 8

FITC Conjugation

A non-limiting example of conjugating FITC with the lipoprotein particles will now be described. To conjugate FITC with the lipoprotein particles, the solution described in Examples 1 and 2 was dialyzed in 0.02M sodium bicarbonate buffer (pH 8.5) that contained 0.15M NaCl. 10 μl of FITC (2 mg/ml) was added to 1 ml of the solution to become covalently coupled to the amines of apoproteins on the surface of the lipoprotein particles. After centrifugation at 7,000 rpm for 20 min, FITC-conjugated lipoprotein particles were obtained, and the supernatant that contain free FITC was discarded.

Example 9

Obtaining Cholesterol-Coated Iron Oxide Nanoparticles Less Than 10 nm Diameter To vary the size of cholesterol-coated iron oxide particles, different concentrations of seeds onto which the cholesterol-coated iron oxide particles grow in size were used. It was observed that the smaller the seed concentration was, the larger was the final size after a certain period of growth.

Iron(III) acetylacetonate (2 mmol) was added to phenyl ether (20 ml) with 1,2-hexadecanediol (10 mmol) and cholic acid (12 mmol) under nitrogen with 1% and 0.1% seed (2 nm cholesterol-coated iron oxide particles). The solutions were then heated in nitrogen to 265° C. for 5 hr. The mixtures were treated with ethanol under air to collect oily particles. The cholesterol-coated iron oxide particles were separated by centrifugation at 20,000 rpm. The separated cholesterol-coated iron oxide particles were suspended in chloroform. The size of cholesterol-coated iron oxide particles varied from 2 nm to 6 nm.

Example 10

Obtaining Cholesterol-Coated Iron Oxide Particles Larger Than 10 nm

Cholesterol-coated iron oxide particles of different cholesterol variety can also be obtained. One example is given here in which the cholesterol has a more strongly hydrophobic tail. Other varieties are also possible. The present example gives cholesterol-coated iron oxide particles of 15 nm.

Figure 6:
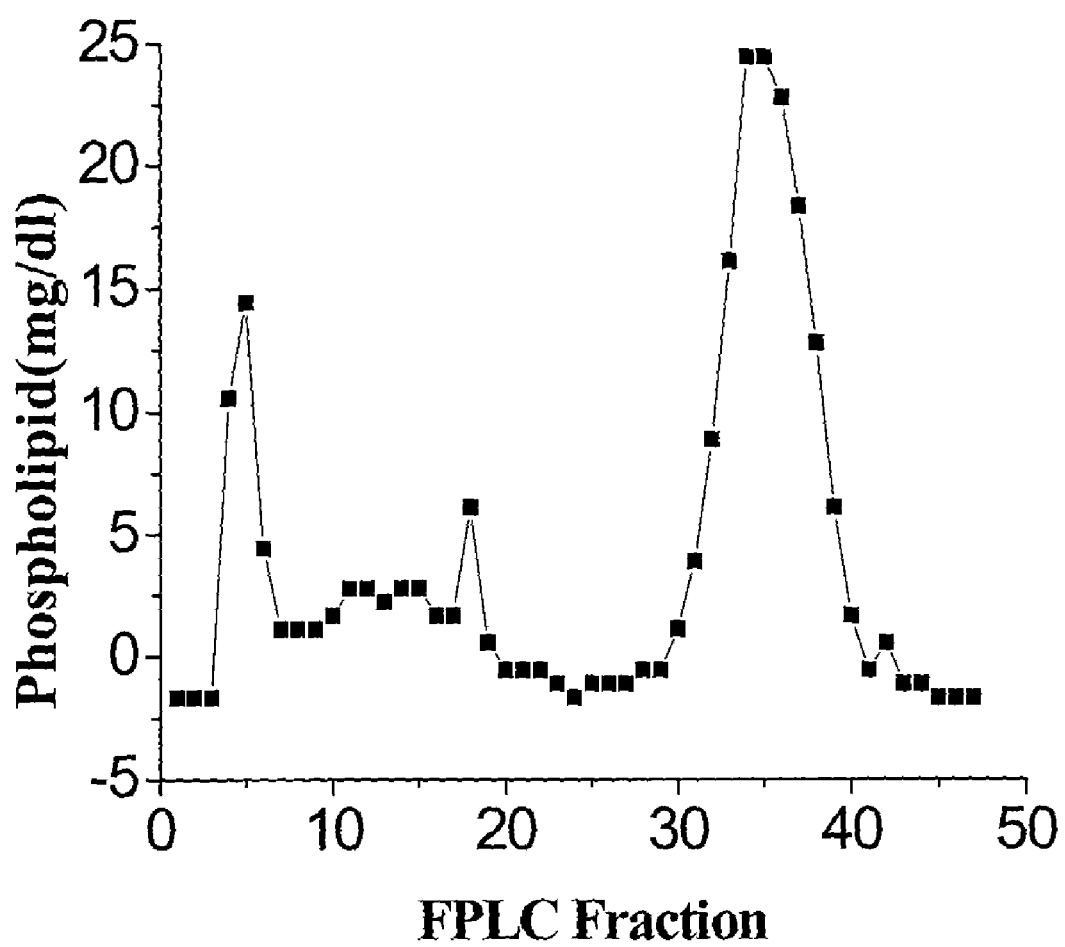
FIG. 6 is a graph demonstrating the co-existence of apo-A1 and phospholipid for cholesterol coated iron oxide-lipoprotein nanoparticles, separated into two main size groups (fractions) by fast protein liquid chromatography (FPLC).

0.1 mol adipoyl chloride was dissolved in 10 ml of dry terahydrofuran (THF) and pyridine (5:1 by volume), and 0.01 mol cholesterol in 10 ml of dry THF. The mixture was reacted in 5 hr at room temperature and then 1 hr at 60° C. under nitrogen, followed by precipitation with water and purification from diethyl ether and hexane (2:1 by volume). Iron(III) acetylacetonate (2 mmol) was added to phenyl ether (20 ml) with 1,2-hexadecanediol (10 mmol) and cholesteryloxycarbonylpentanoic acid (12 mmol) under nitrogen. The solution was then heated in nitrogen to 265° C. for 5 hr. The mixture was treated with ethanol under air to collect oily particles. The cholesterol-coated iron oxide particles were separated by centrifugation at 20,000 rpm (see FIG. 6). The separated cholesterol-coated iron oxide particles were suspended in chloroform.

Example 11

Imaging Fe of IO-Lipoprotein in Cell

After incubation, cholesterol-coated iron oxide-lipoprotein particles can be incorporated into living cells. The locations of cholesterol-coated iron oxide-lipoprotein particles in cells are revealed using Prussian blue staining that highlights Fe (in blue).

Method: 0.1×106 Chinese Hamster ovary cells are seeded into 12-well plate. When the cells reach at near-confluence, the culture medium is removed and cells are washed twice with phosphate buffer solution (PBS). Thereafter, the cells are preincubated (37° C.) for 16 hours in the respective serum-free medium (DMEM) supplemented with 5 mg/mL BSA (Sigma) and antibiotics. After this 16-hour preincubation period, the medium is removed and the cells are washed twice with PBS. The uptake is then initiated by incubation (1.5 hours, 37° C.) of the cells in the respective medium containing BSA (5 mg/mL) and cholesterol-coated iron oxide-lipoprotein particles (the Fe concentration is 10 μgFe/ml). The medium was aspirated and cells are washed twice with PBS followed by analysis and detection. For Prussian blue staining, the cells were fixed with 4% glutaraldehyde, washed, incubated for 30 min with 2% potassium ferrocyanide (Perls' reagent) in 6% HCl, washed, and counterstained with nuclear fast red.

Example 12

Clearing of Cholesterol-Coated Iron Oxide-Lipoprotein Nanoparticles in Blood

Figure 7:
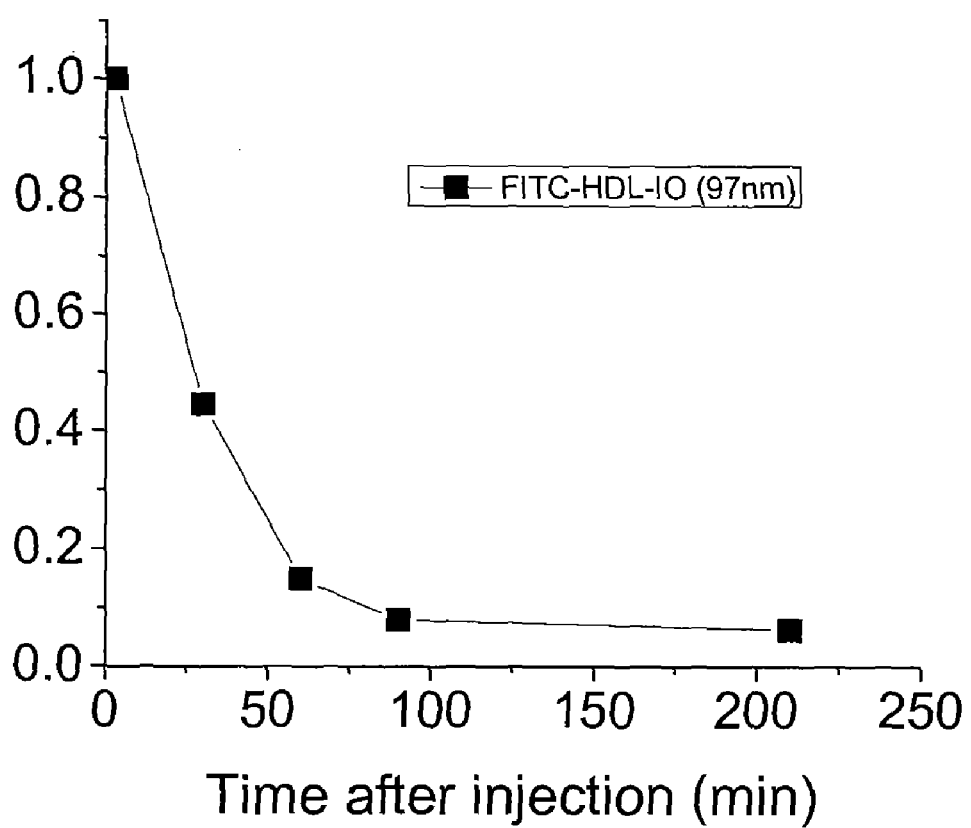
FIG. 7 is a graph demonstrating clearance of cholesterol coated iron oxide-lipoprotein nanoparticles from the blood.

Cholesterol-coated iron oxide-lipoprotein nanoparticles can circulate in blood. Small ones circulate longer while large ones, which are trapped, circulate shorter. For imaging applications, cholesterol-coated iron oxide-lipoprotein particles are typically injected, then cleared from the blood, so that the uptake of cholesterol-coated iron oxide-lipoprotein at specifically targeted sites can be examined without the background signal. A suitable clearing time ranges from several minutes to several days. The cholesterol-coated iron oxide-lipoprotein used in the following experiment contains an additional fluorescent tag, FITC, to facilitate detection (see FIG. 7).

Figure 5:
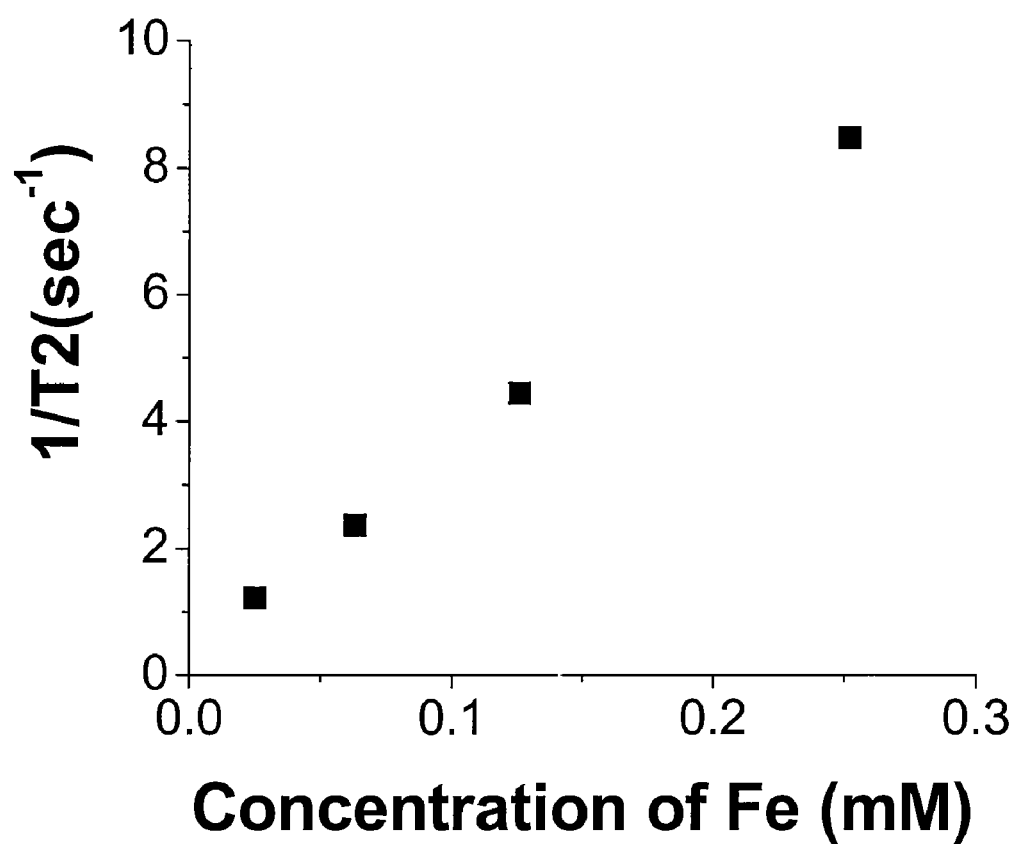
FIG. 5 is a plot of 1/T2 versus iron concentration. T2 is the characteristic relaxation time. Decreasing T2 gives rise to a dark contrast in the MRI image. Concentration of iron (Fe) is calculated from total iron content in micelle solutions.

Method: Fluorescein isothiocyanate (10 mg) was dissolved in 1 ml anhydrous DMSO and 20 μl of the FTIC solution was added to 1 ml of cholesterol-coated iron oxide-lipoprotein (0.5 mg/ml Fe) in 500 mM carbonate buffer solution (pH 9.5). The reaction mixture was reacted at room temperature for 1 hr and dialyzed in a phosphate buffer solution (PBS) to obtain FITC-cholesterol-coated iron oxide-lipoprotein nanoparticles. 200 μl of FITC-cholesterol-coated iron oxide-lipoprotein were injected via the tail vein of mice. FIG. 5 shows the fluorescent signal in the blood samples that were obtained serially over a time over 220 min after injection of the particles into the tail vein. The signals were normalized to the first time point obtained within 2 min of injection. The graph suggests a circulation half-life of about 30 min for a cholesterol-coated iron oxide-lipoprotein particle with a size of 97 nm.

Example 13

T2 and r2 of Cholesterol-Coated Iron Oxide-Lipoprotein Particles of Various Sizes Magnetic sensitivity is characterized by T2 relaxation time, and more specifically, by the Fe-concentration dependence of T2, called r2 (relaxivity). The larger the r2, the better the magnetic sensitivity for MRI. Up to a certain size, there is a tendency for r2 to increase with the size of cholesterol-coated iron oxide-lipoprotein particles. On the other hand, smaller cholesterol-coated iron oxide-lipoprotein particle sizes allow longer circulation and better transport/uptake. Therefore, a wide range of cholesterol-coated iron oxide-lipoprotein particle sizes may be suitable for practical applications. Since cells were not involved in the following experiment, no apoprotein was added to the phopholipid micelle used there.

Method: 0.1~5 ml of egg yolk phosphatidylcholine (20 mg/ml) was added to 10 ml of the above cho-IO (0.1 mg/Fe) suspension and the solution was dried in nitrogen and vacuumed for 2 hr. A phosphate buffer solution (PBS) including 1 mM EDTA and 0.025% NaN3 was added to the dried sample and sonicated for 5 hr at 5° C. to form phospholipid micelle containing a shell of phospholipid and a core of cholesterol-coated iron oxide-lipoprotein particle(s). T2 of the samples was measured by a relaxometer at a magnetic field of 1.5 T.

Figure 8A:
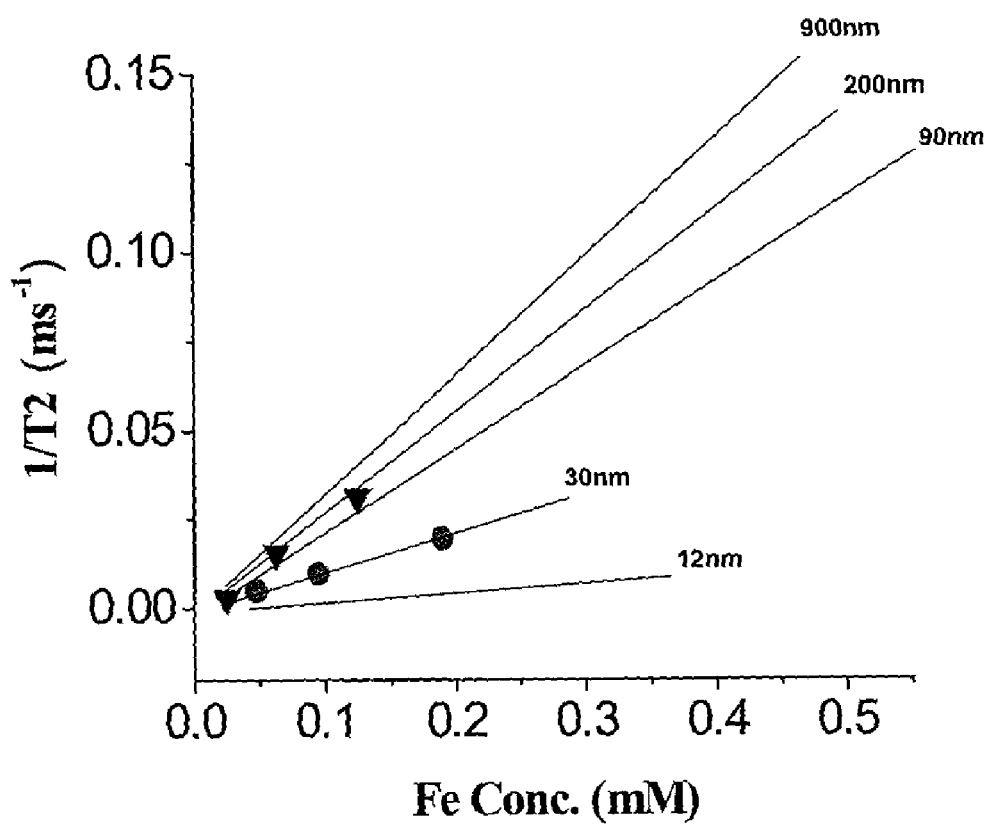
FIGS. 8A and 8B are plots demonstrating size dependence of 1/T2 and r2 (relaxivity) for engineered cholesterol coated iron oxide-HDL lipoprotein nanoparticles in different iron concentration.
Figure 8B:
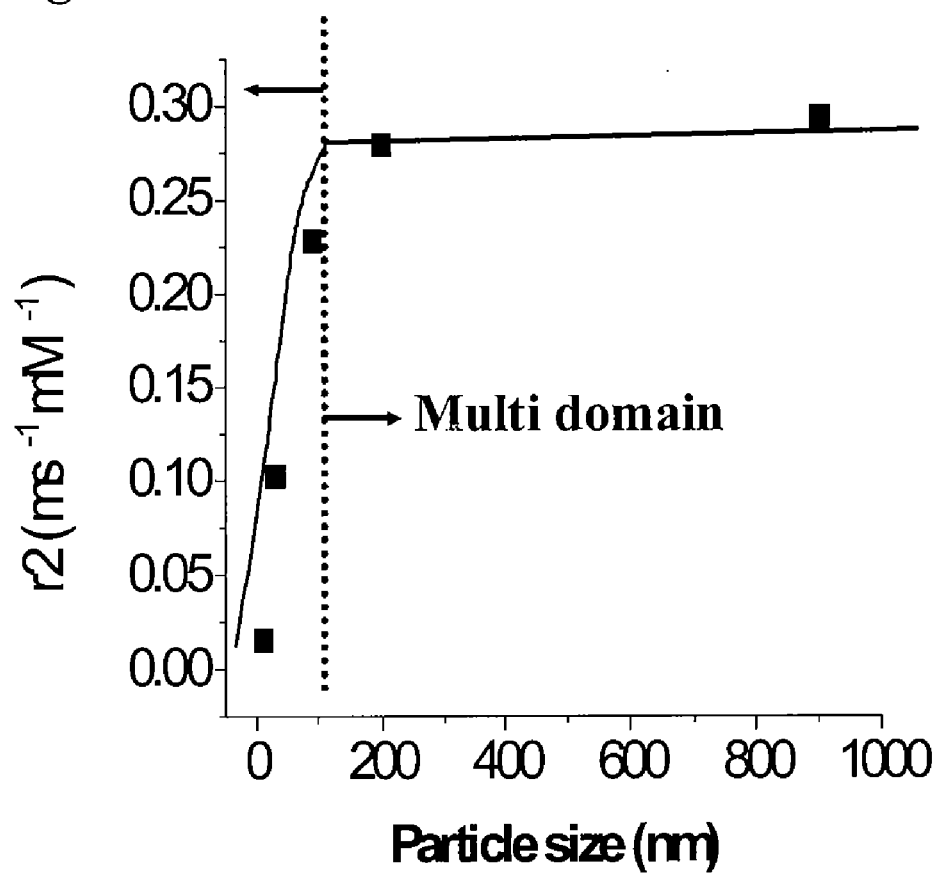

The magnetic property (T2 relaxation) of these particles clearly shows dependence on size as well as on Fe concentration (FIG. 8A). In larger cholesterol-coated iron oxide-lipoprotein particles, beyond 100 nm, cholesterol-coated iron oxide cores are larger consisting of multiple domains of magnetite but their r2 appears to saturate (FIG. 8B).

While the invention has been described in detail and with reference to specific examples thereof, it will be apparent to one skilled in the art that various changes and modifications can be made therein without departing from the spirit and scope thereof.

The invention claimed is:

1. An engineered lipoprotein comprising:
   (a) a core particle or a plurality of core particles, each core particle having (i) an inner part consisting of one or more hydrophilic active agents and a hydrophilic portion of an amphiphilic cholesterol and (ii) an outer part comprising a hydrophobic portion of the amphiphilic cholesterol;
   (b) a layer surrounding the core particle or the plurality of core particles, the layer comprising a phospholipid;
   (c) an apoprotein associated with the layer, and optionally,
   (d) a homing molecule associated with at least one of the apoprotein or the phospholipid.

2. The engineered lipoprotein of claim 1, wherein the one or more hydrophilic active agents are a diagnostic agent.

3. The engineered lipoprotein of claim 2, wherein the diagnostic agent is a magnetic resonance imaging (MRI) contrast agent.

4. The engineered lipoprotein of claim 3, wherein the MRI contrast agent comprises Fe, Co, Mn, Ni, or Cr.

5. The engineered lipoprotein of claim 4, wherein the MRI contrast agent is iron oxide.

6. The engineered lipoprotein of claim 1, wherein the hydrophilic portion of the amphiphilic cholesterol is at least one of (a) an anionic group selected from at least one of sulfate, sulfonate or carboxylate anions, (b) a cationic group selected from at least one of quaternary ammonium cations, or (c) a hydrophilic nonionic group selected from at least one of poly(ethylene glycol), alkyl poly(ethylene oxide) and alkyl poly(glucoside).

7. The engineered lipoprotein of claim 6, wherein the amphiphilic cholesterol is a member selected from the group consisting of cholesteryl 3β-N-(dimethylaminoethyl)carbamate hydrochloride, cholic acid, 3-cholesteryloxycarbonyl pentanoic acid, cholesterol-poly(ethylene glycol), cholesterol-poly(ethylene oxide) and cholesterol-poly(glucoside).

8. The engineered lipoprotein of claim 1, wherein the phospholipid is a member selected from the group consisting of phosphatidylcholine, phosphatidylethanolamine, phosphatidylserine, phosphatidylinositol, phosphatidic acid, phosphatidylglycerol, and cardiolipin.

9. The engineered lipoprotein of claim 1, wherein the apoprotein is a member selected from the group consisting of apoprotein A1, A2, A4, B48, B100, C1, C2, C3, D, and E.

10. The engineered lipoprotein of claim 1, wherein the inner part of the core particle consists of a plurality of hydrophilic active agents and a hydrophilic portion of an amphiphilic cholesterol.

* * * * *